US012599671B2

(12) United States Patent
Li et al.

(10) Patent No.: US 12,599,671 B2
(45) Date of Patent: Apr. 14, 2026

(54) COMPOUNDS, COMPOSITIONS, AND METHODS FOR PROTEIN DEGRADATION

(71) Applicant: DANA-FARBER CANCER INSTITUTE, INC., Boston, MA (US)

(72) Inventors: Deyao Li, Quincy, MA (US); Lingling Dai, Medford, MA (US); Jun Qi, Sharon, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 808 days.

(21) Appl. No.: 17/799,000

(22) PCT Filed: Feb. 11, 2021

(86) PCT No.: PCT/US2021/017626

§ 371 (c)(1),
(2) Date: Aug. 11, 2022

(87) PCT Pub. No.: WO2021/163302

PCT Pub. Date: Aug. 19, 2021

(65) Prior Publication Data

US 2023/0096160 A1 Mar. 30, 2023

Related U.S. Application Data

(60) Provisional application No. 62/975,529, filed on Feb. 12, 2020.

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
CPC ...................................................... A61K 47/55
See application file for complete search history.

(56) References Cited

U.S. PATENT DOCUMENTS

| | | | | |
|---|---|---|---|---|
| 2017/0121321 | A1 | 5/2017 | Crews et al. | |
| 2018/0134684 | A1 * | 5/2018 | Bradner .................. | A61P 37/00 |
| 2018/0140578 | A1 | 5/2018 | Nijhawan et al. | |
| 2018/0147202 | A1 | 5/2018 | Crew et al. | |
| 2019/0300521 | A1 | 10/2019 | Crew et al. | |

FOREIGN PATENT DOCUMENTS

| | | | |
|---|---|---|---|
| WO | 2017223415 | A1 | 12/2017 |
| WO | 2019207538 | A1 | 10/2019 |

OTHER PUBLICATIONS

Papillon, "Discovery of Orally Active Inhibitors of Brahma Homolog (BRM)/SMARCA2 ATPase Activity for the Treatment of Brahma Related Gene 1 (BRG1)/SMARCA4-Mutant Cancers", J. Med. Chem, 2018, vol. 61, pp. 10155-10172.*
Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
Registry/Zregistry (CAS REGISTRYSM) Sep. 2016 2 pages.*
Scheespstr "Bivalent Ligands for Protein Degradation in Drug Discovery", Computational and St.*
Papillon, J. Med. Chem. 2018, 61, 10155-10172.*
Scheepstra, Computational and Structural Biotechnology Journal 17 (2019) 160-176.*
Arthur, Explor Target Antitumor Ther. 2020;1:131-52.*
Wang, Acta Pharmaceutica Sinica B 2020;10(2):207e238.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Zoppi et al., "Iterative Design and Optimization of Initially Inactive Proteolysis Targeting Chimeras (PROTACs) Identify VZ195 as a Potent, Fast, and Selective von Hippel-Lindau (VHL) Based Dual Degrader Prober of BRD9 and BRD7", J. Med. Chem., 2019, vol. 62, pp. 699-726.
Papillon, J., et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers", J. Med. Chem, 2018, vol. 61, pp. 10155-10172.
Scheepstra, M., et al., "Bivalent Ligands for Protein Degradation in Drug Discovery", Computational and Structural Biotechnology Journal 17, 2019, pp. 160-176.
Bondeson, D. P. et al., "Lessons in PROTAC design from selective degradation with a promiscuous warhead", Cell Chem. Biol., 2018, vol. 25, No. 1, pp. 78-87.
Li, X. et al., "Proteolysis-targeting chimera (PROTAC) for targeted protein degradation and cancer therapy", J. Hematol. Oncol., 2020, vol. 13, No. 50, 14 pages.
Tan, L. et al., "When Kinases Meet PROTACS", Chin. J. Chem., 2018, vol. 36, pp. 971-977.

* cited by examiner

*Primary Examiner* — Nizal S Chandrakumar
(74) *Attorney, Agent, or Firm* — ArentFox Schiff LLP; Daniel W. Clarke; Shawn P. Foley

(57) ABSTRACT

Disclosed herein are compounds that target SMARCA2, SMARCA4 or BRM, causing their degradation. Also disclosed herein are compositions and methods of use in treating associated disorders and diseases.

17 Claims, 9 Drawing Sheets cmp12

Cmp14

COMPOUNDS, COMPOSITIONS, AND METHODS FOR PROTEIN DEGRADATION

RELATED APPLICATIONS

This application is a U.S. national stage application, filed under 35 U.S.C. § 371, of International Application No. PCT/US2021/017626, filed Feb. 11, 2021, which claims the benefit of priority under 35 U.S.C. § 119(e) to U.S. Provisional Patent Application No. 62/975,529, filed on Feb. 12, 2020, the contents of each of which are hereby incorporated by reference in their entirety.

BACKGROUND

Transcription aberrant regulation through defects in chromatin-remodeling activity plays an important role in tumorigenesis. Tumor-exomesequencing studies have shown that multi-subunit SWI/SNF chromatin-remodeling complexes are mutated in approximately 20% of human cancers and contain one of two mutually exclusive ATPases, SMARCA2 or SMARCA4. Previous studies revealed a synthetic lethal relationship between SMARCA2 and SMARCA4, in which SMARCA2 is highly dependent in SMARCA4-deficient cancer cells. SMARCA4 mutation or expression loss occurs in many cancers, such as non-small cell lung cancers. Furthermore, the interruption of SMARCA2 using biological methods, such as knock out or knock down, is lethal to cancer cells. Thus, the targeted degradation of SMARCA2 or SMARCA4 represents an attractive method for the treatment of many cancers. However, to date, there are no small molecule treatments that target SMARCA2 or SMARCA4 and are approved for use in humans.

SUMMARY OF THE INVENTION

In certain embodiments, the disclosure provides compounds of Formula I.

I

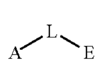

or a pharmaceutically acceptable salt thereof, wherein A is

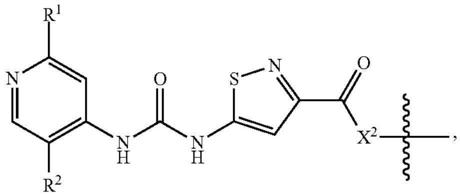

,

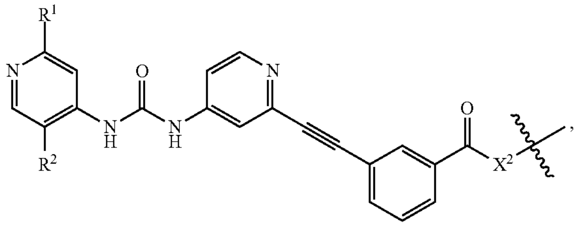

,

-continued

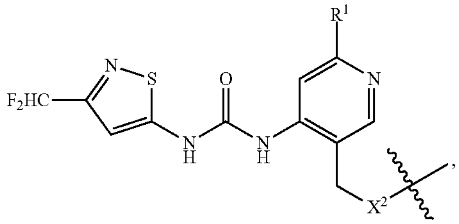

,

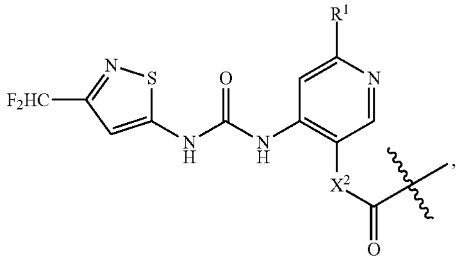

,

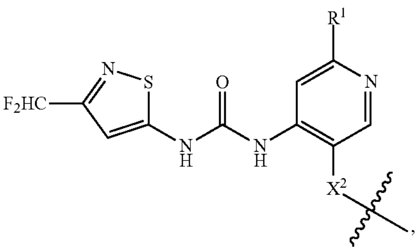

, or

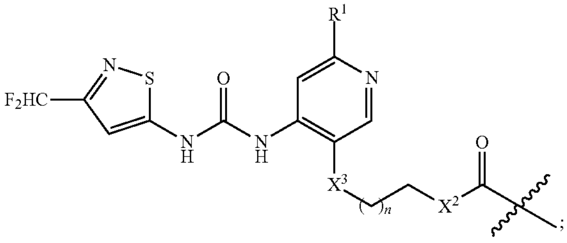

;

E is

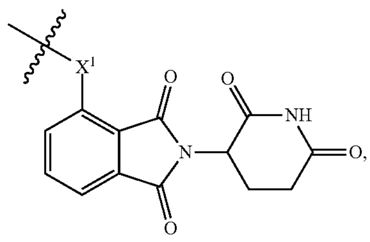

,

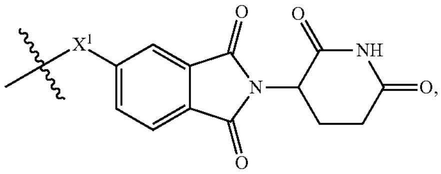

,

-continued

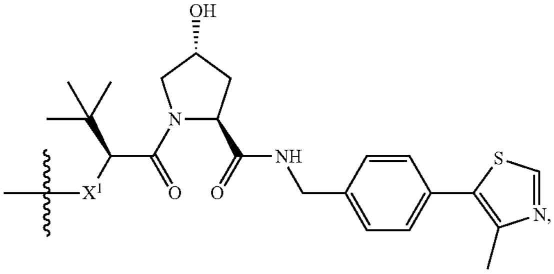

,

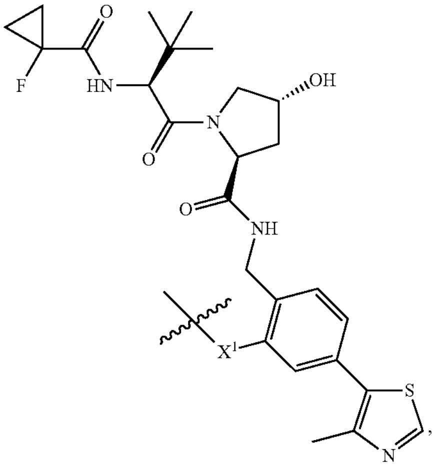

,

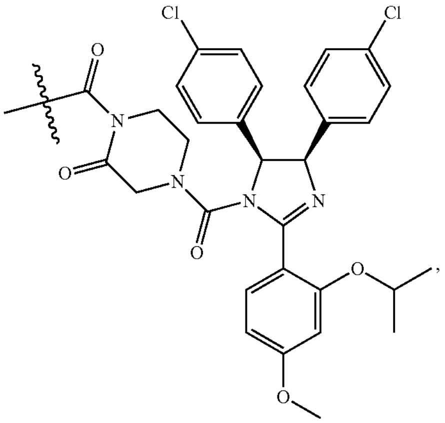

,

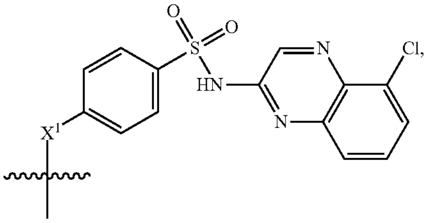

or

-continued

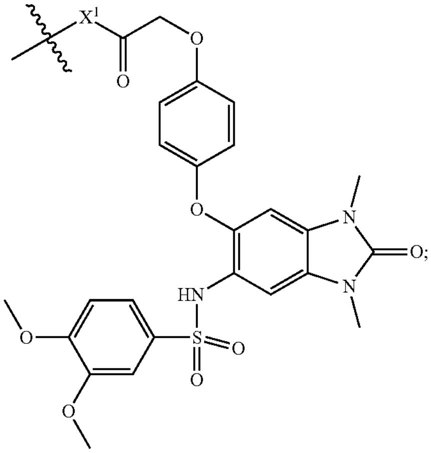

;

$X^1$ and $X^2$ are each independently selected from O, $NR^3$, and S; or $X^1$ or $X^2$ combine with L to form a heterocyclyl or heteroaryl; or both of $X^1$ and $X^2$ combine with L to form a heterocyclyl or heteroaryl;

$X^3$ is O, $NR^3$, or S;

L comprises an alkylene, alkenylene, alkynylene, cycloalkylene, heterocyclylene, arylene, or heteroarylene chain, or a combination thereof, comprising 1 to 35 carbon atoms, for example, 1 to 35 —$CH_2$— moieties, optionally wherein:

if L comprises an alkylene comprising 1 to 35 —$CH_2$— moieties, then at least one, but no more than ten, —$CH_2$— moieties of L are independently replaced with a moiety selected from —C(═O)—, —C(═O)—$NR^4$—, —$NR^4$—C(═O)—, —C(═O)—O—, —O—C(═O)—, —$NR^4$—C(═O)—$NR^3$—, —O—C(═O)—$NR^4$—, —$NR^4$—C(═O)—O—, —O—, —S—, and —$NR^4$—, provided that the number of —$CH_2$— moieties of L is larger than the collective number of —C(═O)—, —C(═O)—$NR^4$—, —$NR^4$—C(═O)—, —C(═O)—O—, —O—C(═O)—, —$NR^4$—C(═O)—$NR^3$—, —O—C(═O)—$NR^4$—, —$NR^4$—C(═O)—O—, —O—, —S—, and —$NR_3$— moieties of L, and provided there is at least one —$CH_2$— between each —C(═O)—, —C(═O)—$NR^4$—, —$NR^4$—C(═O)—, —C(═O)—O—, —O—C(═O)—, —$NR^4$—C(═O)—$NR_3$—, —O—C(═O)—$NR^4$—, —$NR^4$—C(═O)—O—, —O—, —S—, and —$NR^4$— moiety of L;

$R^1$ and $R^2$ are each independently selected from H, alkyl, halo, hydroxyl, hydroxalkyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, and aralkyl;

$R^3$ and $R^4$ are each independently selected from H and alkyl; and n is 1-5, preferably 1.

In other aspects, the disclosure provides a composition comprising a compound of formula I and at least one pharmaceutically acceptable excipient.

In yet other aspects, the disclosure provides methods treating a disease or disorder (e.g., cancer) comprising administering to a subject in need thereof a compound of formula I.

DETAILED DESCRIPTION OF THE INVENTION

Figure 1A:
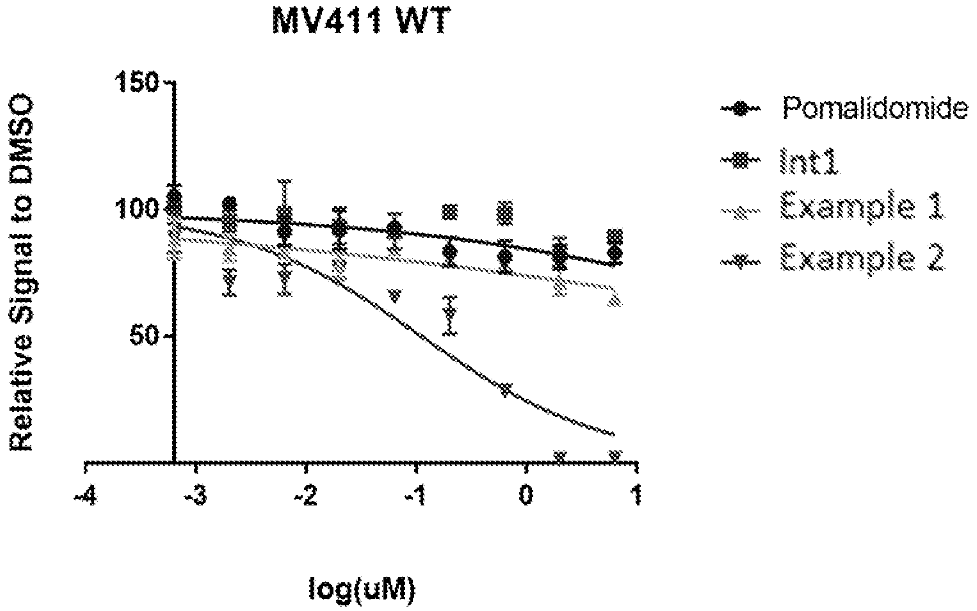
FIG. 1A is a graph showing the activity of exemplary compounds of the disclosure vs. certain reference compounds against MV411 WT.
Figure 1B:
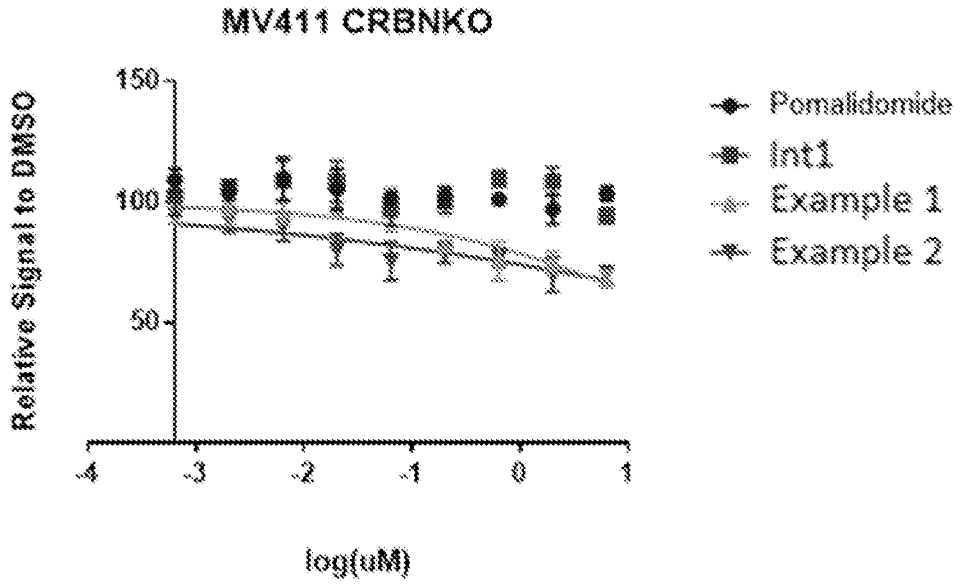
FIG. 1B is a graph showing the activity of exemplary compounds of the disclosure vs. certain reference compounds against MV411 CRBN knock out.
Figure 2A:
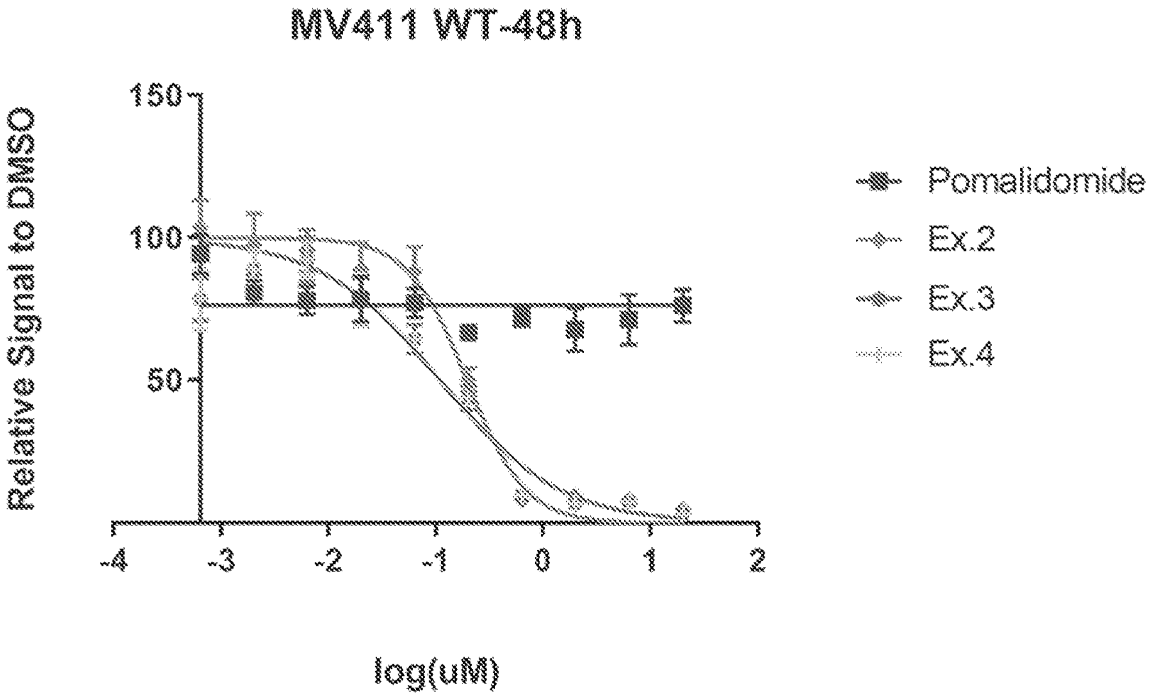
FIG. 2A is a graph showing the activity of exemplary compounds of the disclosure vs. certain reference compounds against MV411 WT after 48 hours.
Figure 2B:
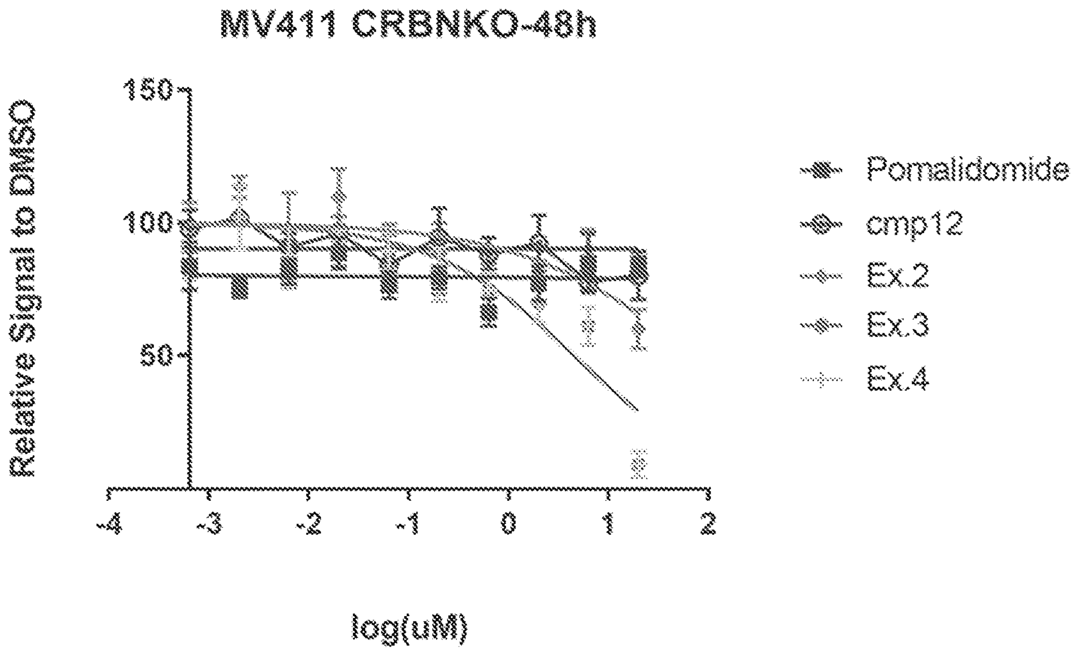
FIG. 2B is a graph showing the activity of exemplary compounds of the disclosure vs. certain reference compounds against MV411 CRBN knock out after 48 hours.
Figure 3A:
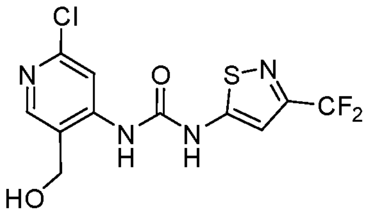
FIG. 3A is a structural representation of Cmp12.
Figure 3B:
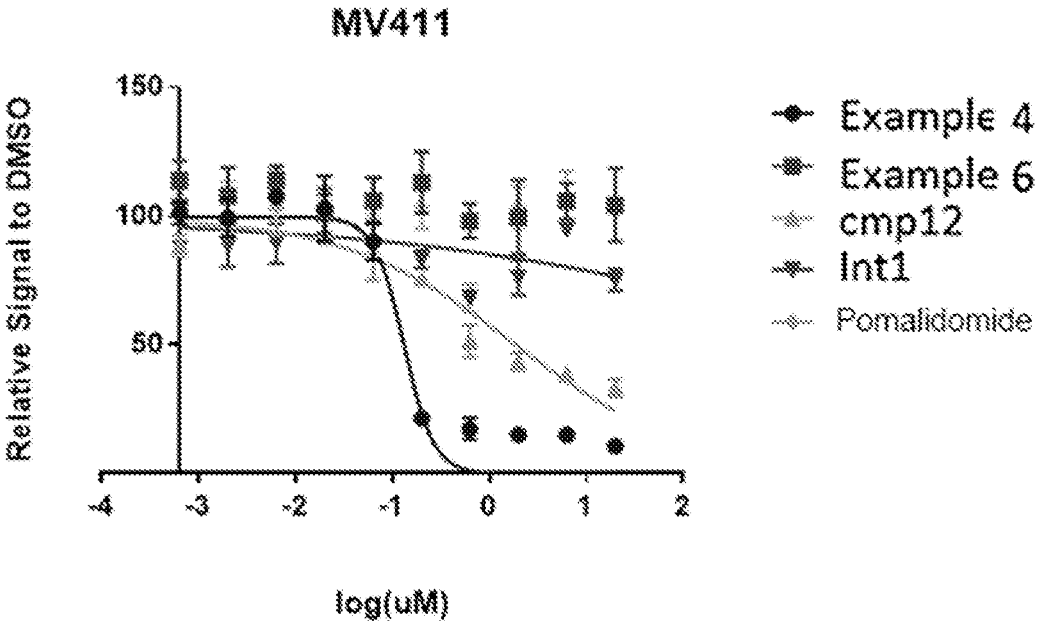
FIG. 3B is a graph showing the activity of exemplary compounds of the disclosure against MV411 vs. certain reference compounds.
Figure 3C:
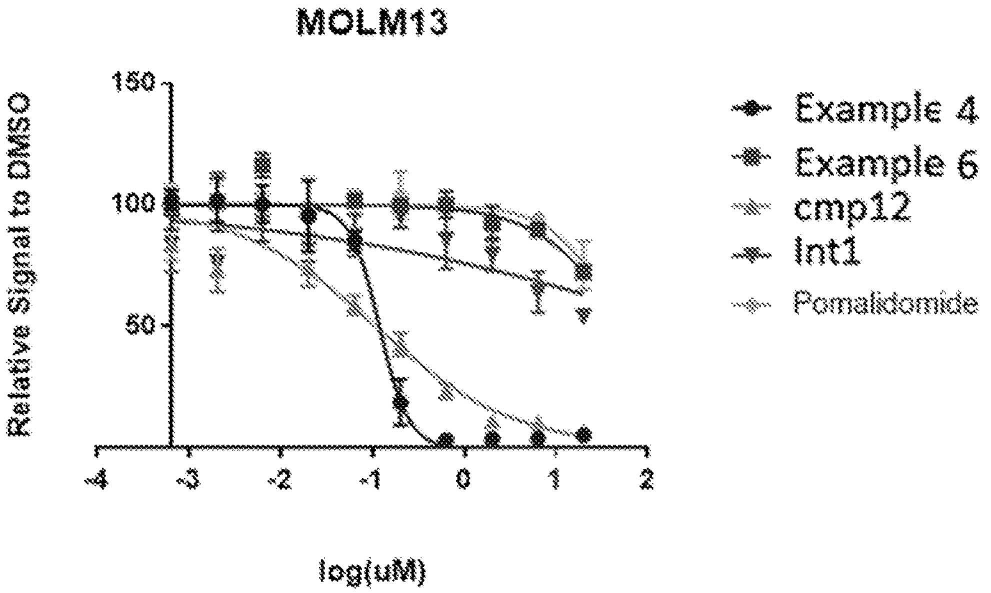
FIG. 3C is a graph showing the activity of exemplary compounds of the disclosure against MOLM13 vs. certain reference compounds.
Figure 4A:
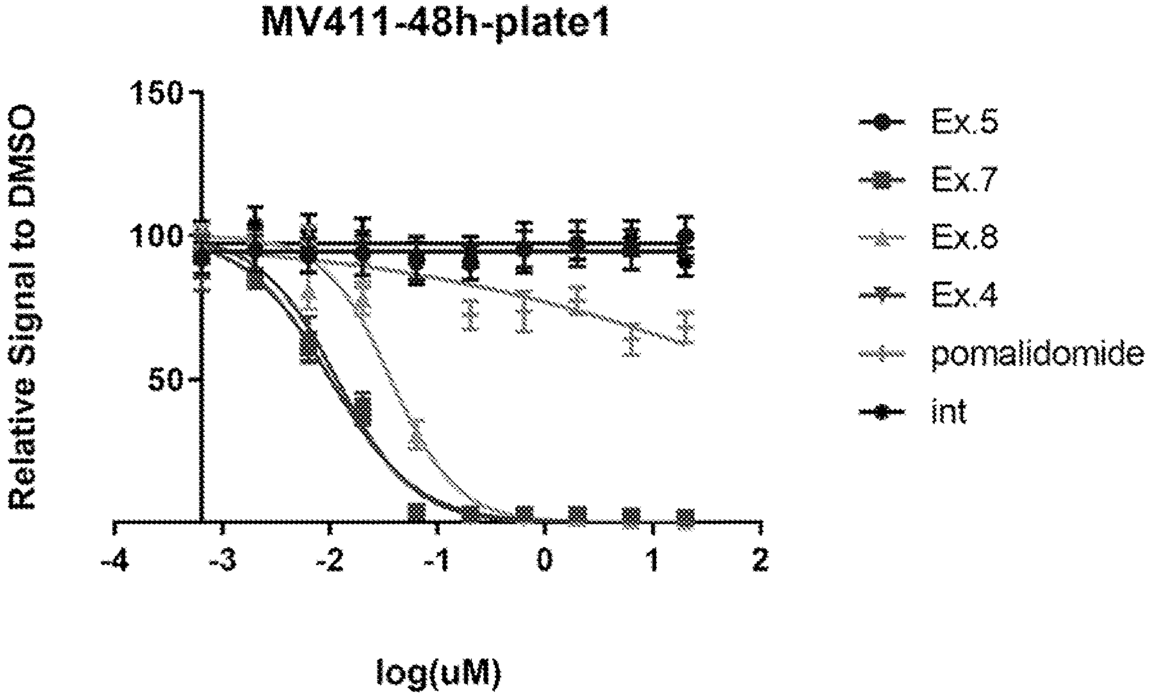
FIG. 4A is a graph showing the activity of exemplary compounds of the disclosure vs. certain reference compounds against MV411 after 48 hours.
Figure 4B:
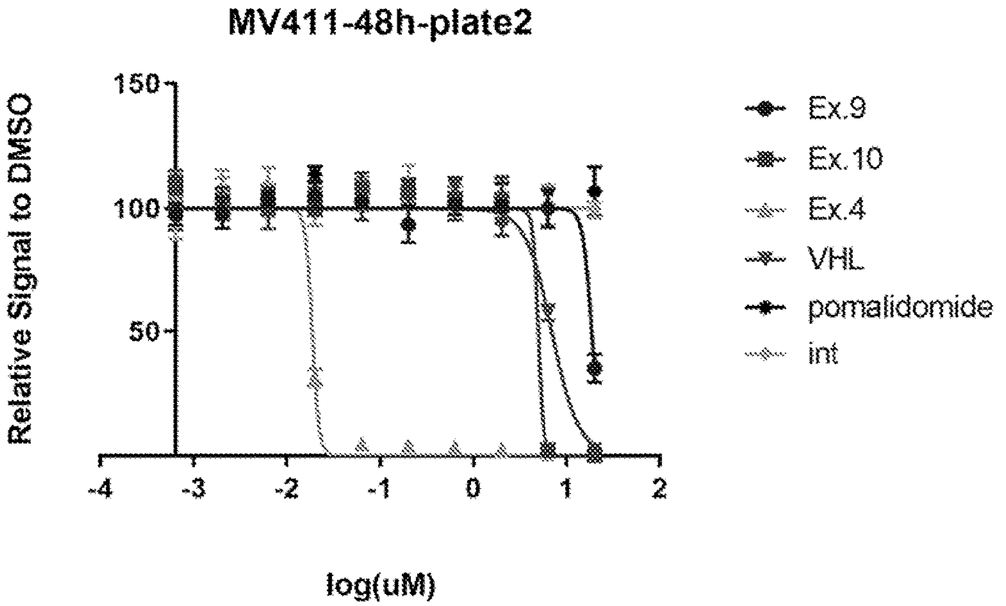
FIG. 4B is a graph showing the activity of exemplary compounds of the disclosure vs. certain reference compounds against MV411 after 48 hours.
Figure 5A:
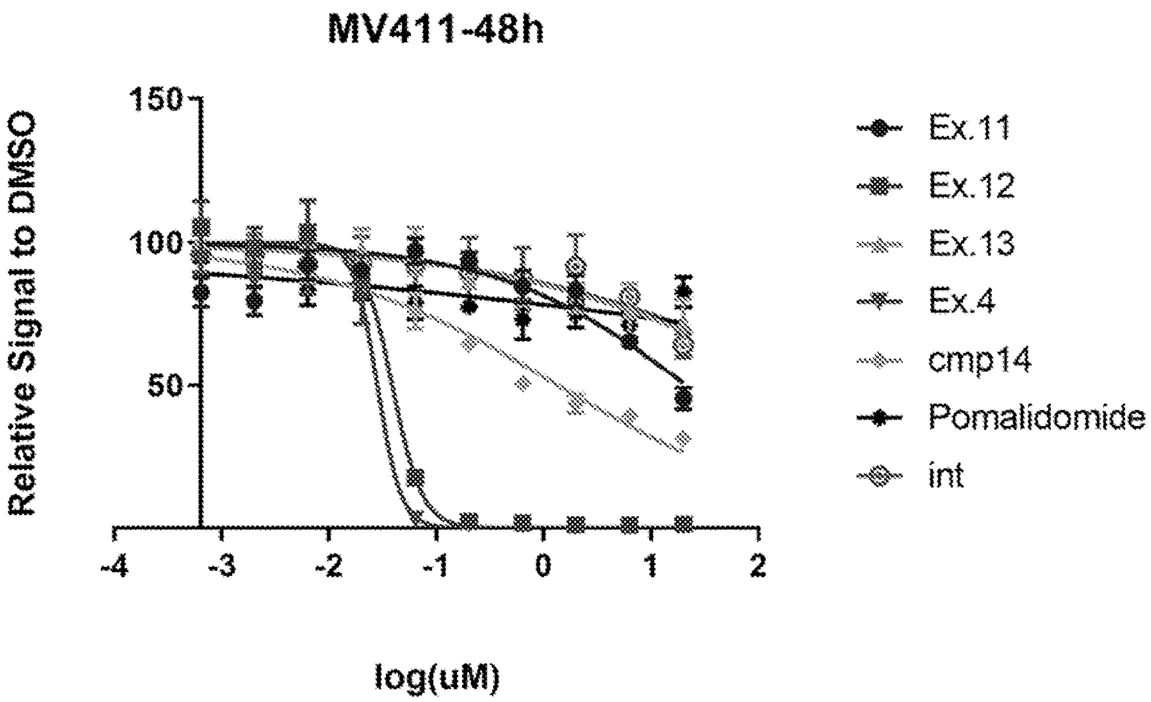
FIG. 5A is a graph showing the activity of exemplary compounds of the disclosure vs. certain reference compounds against MV411 after 48 hours.
Figure 5B:
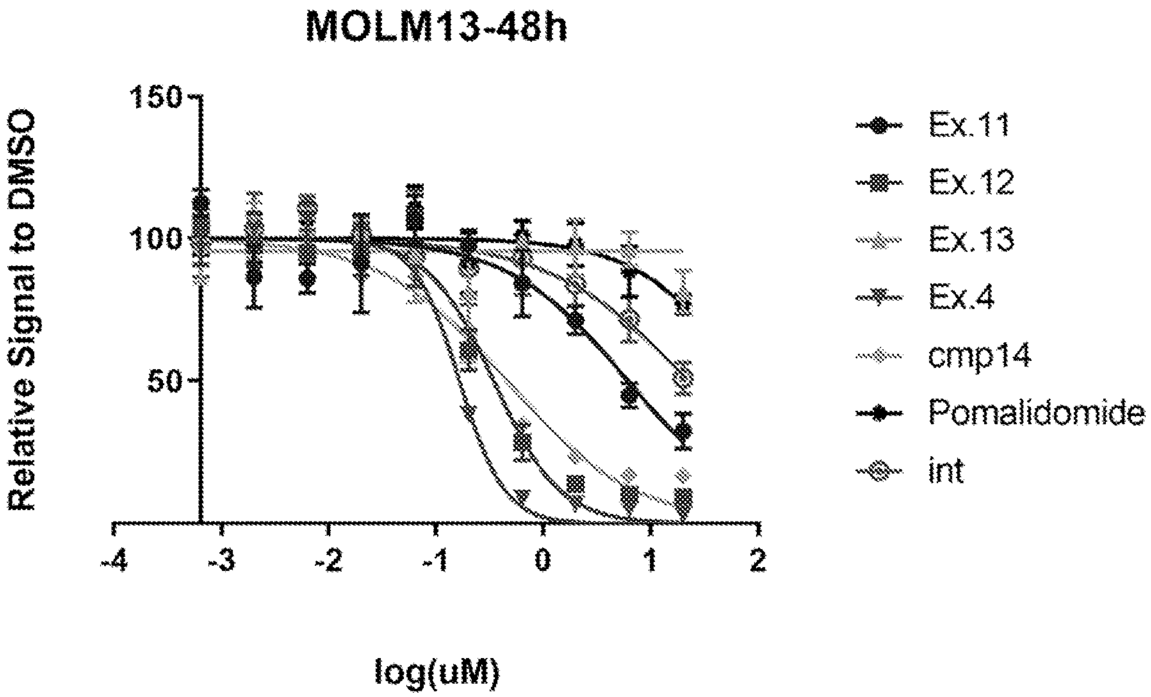
FIG. 5B is a graph showing the activity of exemplary compounds of the disclosure vs. certain reference compounds against MOLM after 48 hours.
Figure 6A:
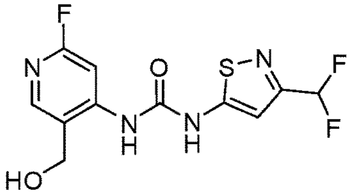
FIG. 6A is a structural representation of Cmp14.
Figure 6B:
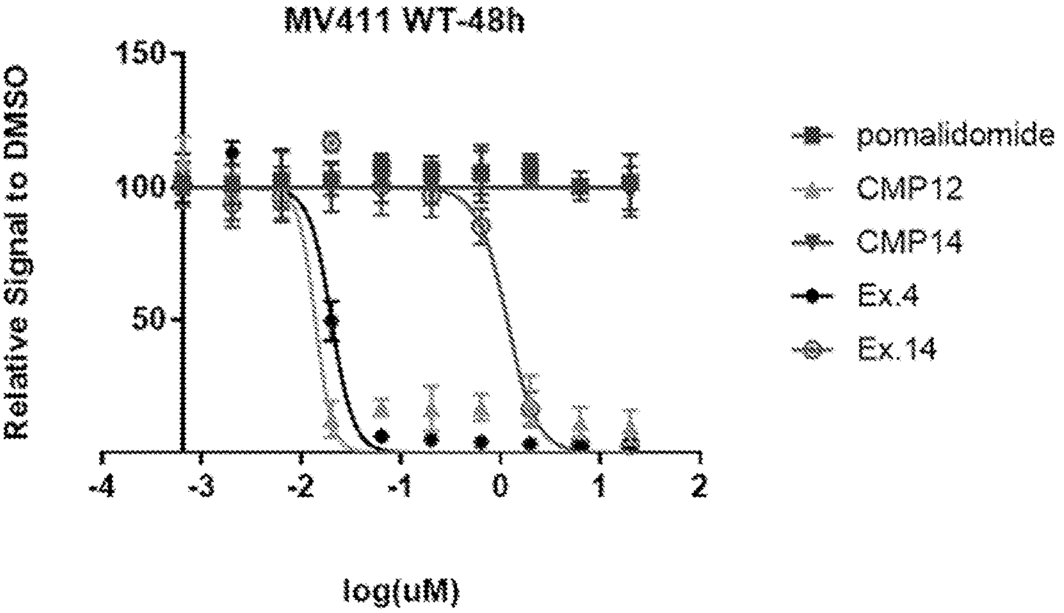
FIG. 6B is a graph showing the activity of exemplary compounds of the disclosure vs. certain reference compounds against MV411 WT after 48 hours.
Figure 6C:
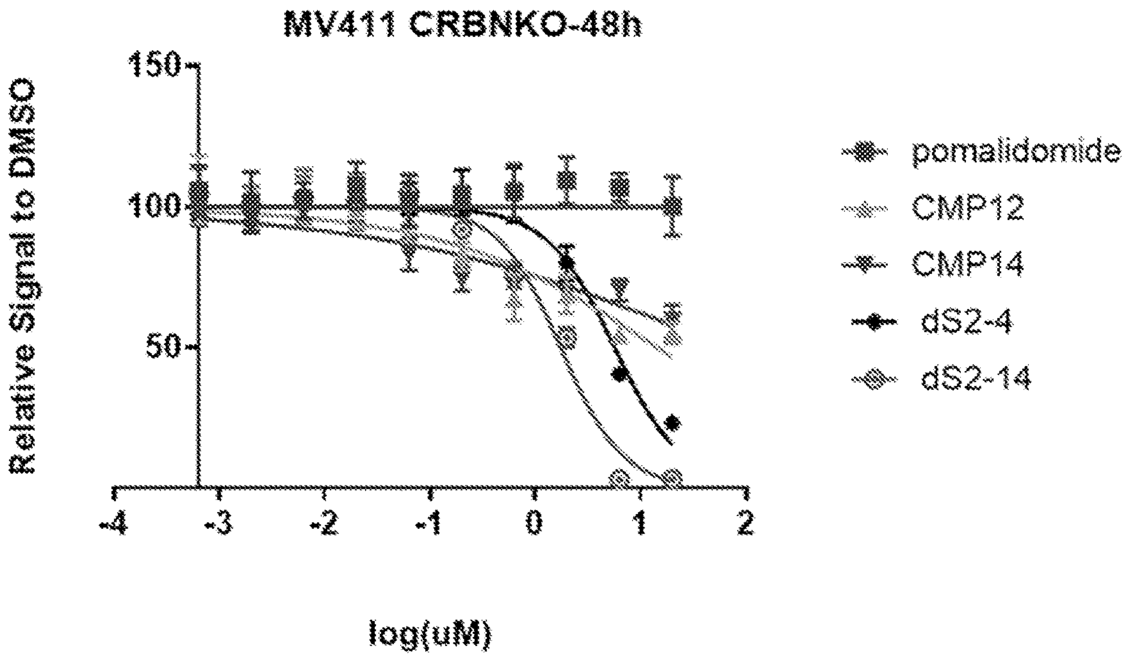
FIG. 6C is a graph showing the activity of exemplary compounds of the disclosure vs. certain reference compounds against MV411 CRBN knock out after 48 hours.
Figure 7A:
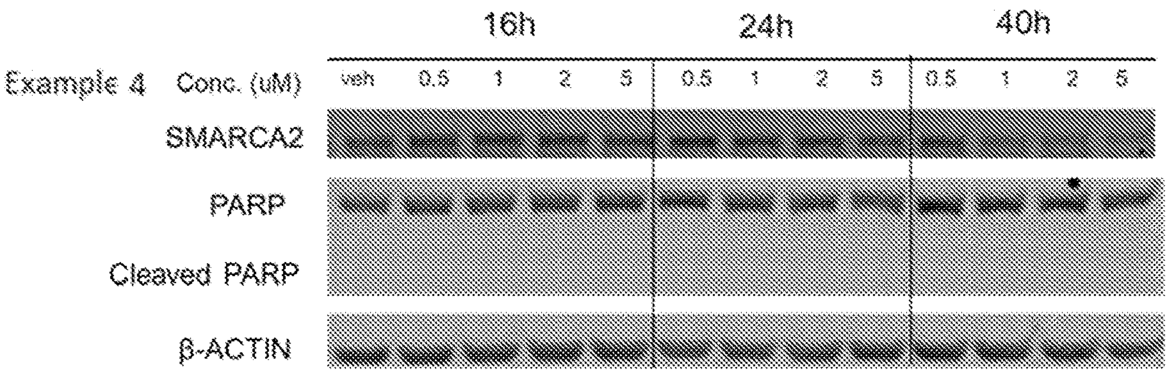
FIG. 7A is a Western Blot of A549 cells treated with Example 4 at a concentration of 1 μM. The cells started to exhibit protein degradation after 40 hours.
Figure 7B:
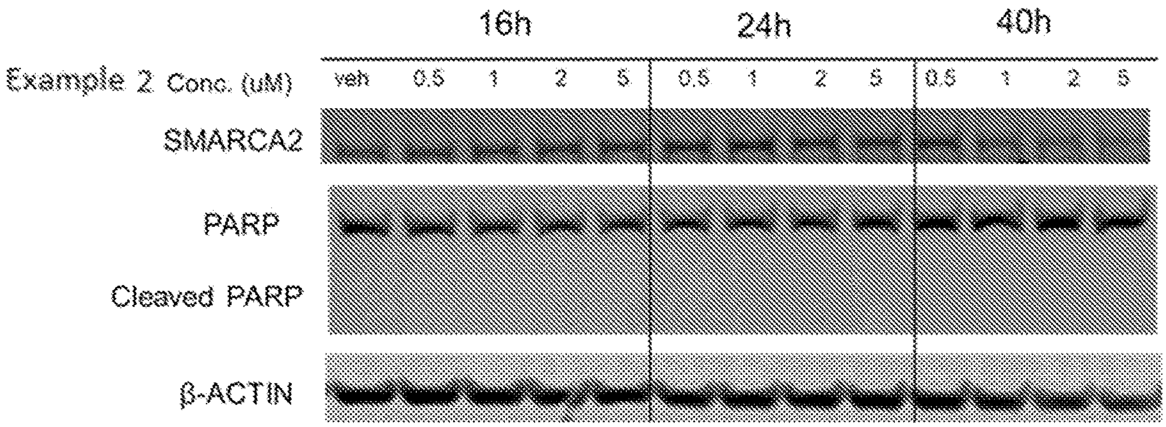
FIG. 7B is a Western Blot of A549 cells treated with Example 2 at a concentration of 1 μM. The cells started to exhibit protein degradation after 40 hours.
Figure 7C:
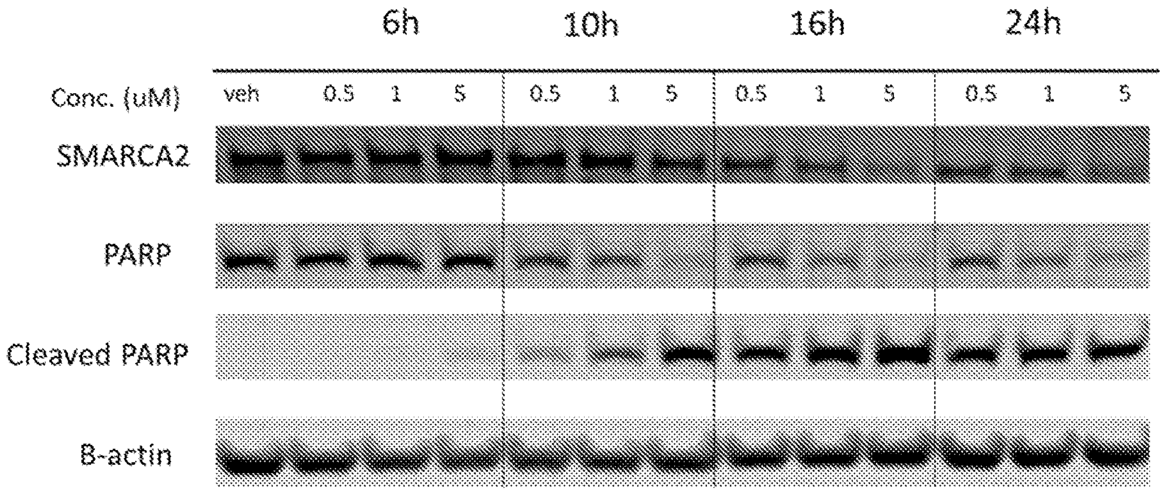
FIG. 7C is a Western Blot of MOLM13 cells treated with Example 4. The cells started to exhibit protein degradation after 16 hours.

Proteolysis targeting chimeras (PROTACs) are a class of drug molecules wherein a target-binding ligand is linked covalently to an E3 ligase-binding ligand that can form a target-PROTAC-ligase ternary complex. The ternary complex directs the ubiquitin proteasome system to degrade the target protein.

PROTACs have shown higher degrees of selectivity for protein degradation than the target ligand itself and have thus expanded the druggable proteome, as degradation is not limited to the protein domain functionally responsible for the disease. Disclosed herein are PROTACS that target certain proteins, such as the core catalytic subunit SMARCA2, to interrupt the function of SWI/SNF complex in cancer cell.

Exemplary Compounds of the Disclosure

In certain embodiments, the disclosure provides compounds of Formula I.

I or a pharmaceutically acceptable salt thereof, wherein A is

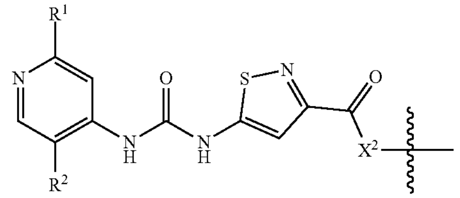

,

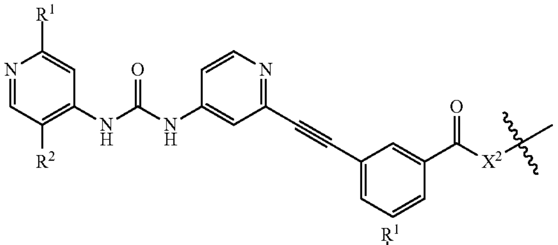

,

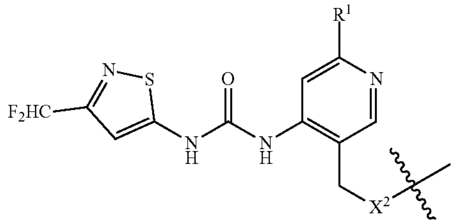

,

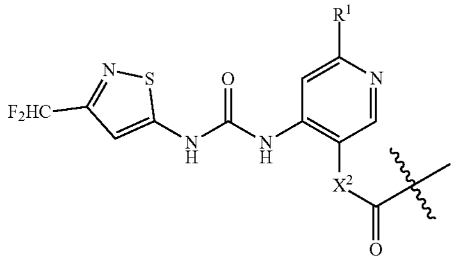

,

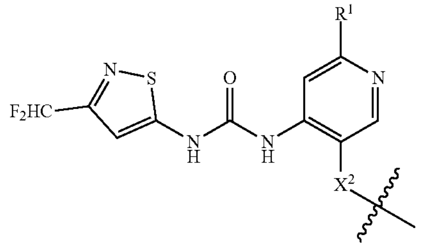

, or

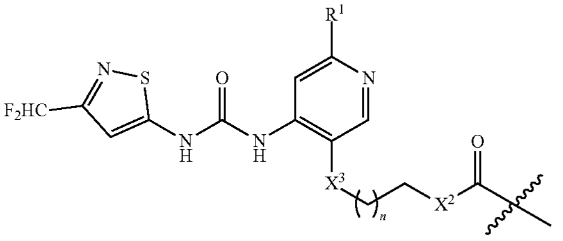

;

E is

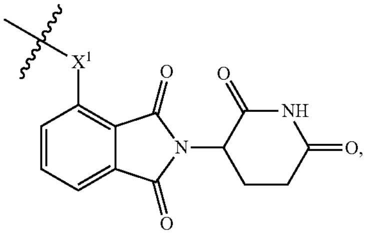

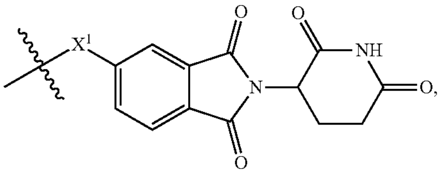

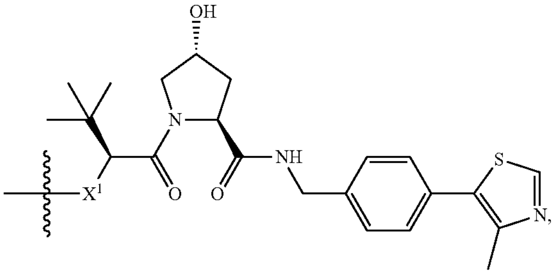

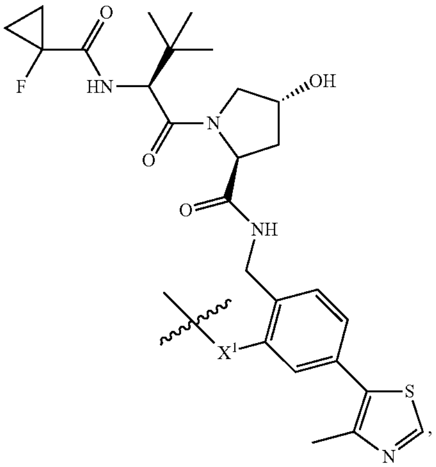

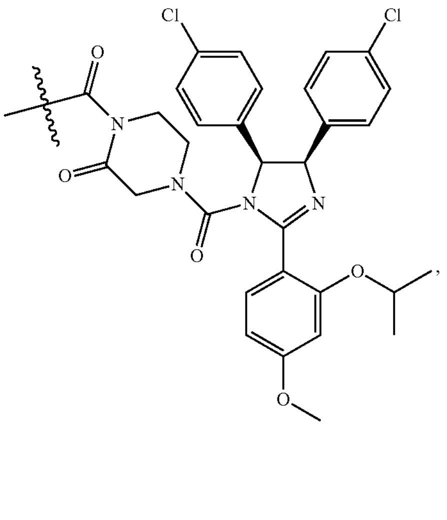

-continued

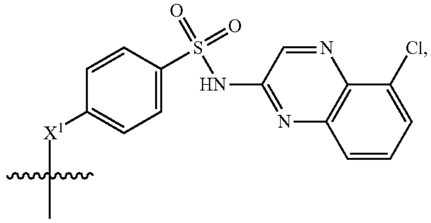

or

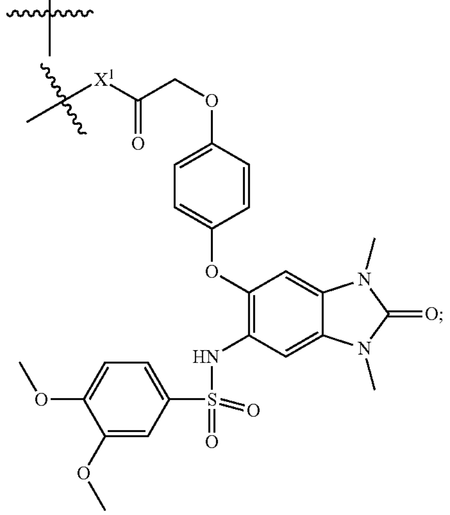

$X^1$ and $X^2$ are each independently selected from O, $NR^3$, and S; or $X^1$ or $X^2$ combine with L to form a heterocyclyl or heteroaryl; or both of $X^1$ and $X^2$ combine with L to form a heterocyclyl or heteroaryl;

$X^3$ is O, $NR^3$, or S;

L comprises an alkylene, alkenylene, alkynylene, cycloalkylene, heterocyclylene, arylene, or heteroarylene chain, or a combination thereof, comprising 1 to 35 carbon atoms, for example, 1 to 35 —$CH_2$— moieties, optionally wherein:

if L comprises an alkylene comprising 1 to 35 —$CH_2$— moieties, then at least one, but no more than ten, —$CH_2$— moieties of L are independently replaced with a moiety selected from —C(═O)—, —C(═O)—$NR^4$—, —$NR^4$—C(═O)—, —C(═O)—O—, —O—C(═O)—, —$NR^4$—C(═O)—$NR^3$—, —O—C(═O)—$NR^4$—, —$NR^4$—C(═O)—O—, —O—, —S—, and —$NR^4$—, provided that the number of —$CH_2$— moieties of L is larger than the collective number of —C(═O)—, —C(═O)—$NR^4$—, —$NR^4$—C(═O)—, —C(═O)—O—, —O—C(═O)—, —$NR^4$—C(═O)—$NR^3$—, —O—C(═O)—$NR^4$—, —$NR^4$—C(═O)—O—, —O—, —S—, and —$NR^3$— moieties of L, and provided there is at least one —$CH_2$— between each —C(═O)—, —C(═O)—$NR^4$—, —$NR^4$—C(═O)—, —C(═O)—O—, —O—C(═O)—, —$NR^4$—C(═O)—$NR^3$—, —O—C(═O)—$NR^4$—, —$NR^4$—C(═O)—O—, —O—, —S—, and —$NR^4$— moiety of L;

$R^1$ and $R^2$ are each independently selected from H, alkyl, halo, hydroxyl, hydroxalkyl, carboxyl, acyl, ester, thioester, alkoxy, phosphoryl, amino, amido, cyano, nitro, azido, alkylthio, alkenyl, alkynyl, cycloalkyl, heterocyclylalkyl, heteroaralkyl, sulfonamide, aryl, heteroaryl, heterocyclyl, and aralkyl;

$R^3$ and $R^4$ are each independently selected from H and alkyl; and n is 1-5, preferably 1.

In certain embodiments of formula I, $R^1$ is halo. In certain embodiments, $R^1$ is fluoro. In certain preferred embodiments, $R^1$ is chloro.

In certain embodiments of formula I, $R^2$ is H or hydroxyalkyl. In certain preferred embodiments, $R^2$ is H.

In certain embodiments of formula I, $R^1$ and $R^2$ are not both H.

In certain embodiments of formula I, $R^3$ is H.

In certain embodiments of formula I, $R^4$ is H.

In certain embodiments of formula I, the compound is:

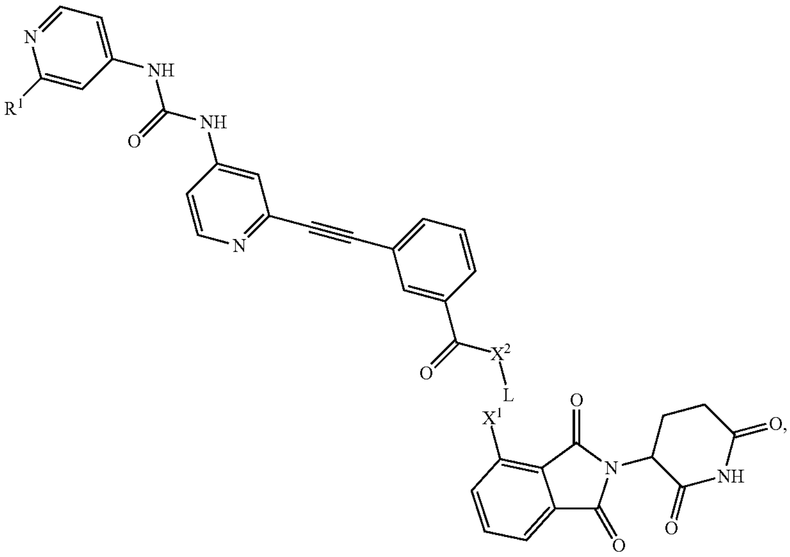
,

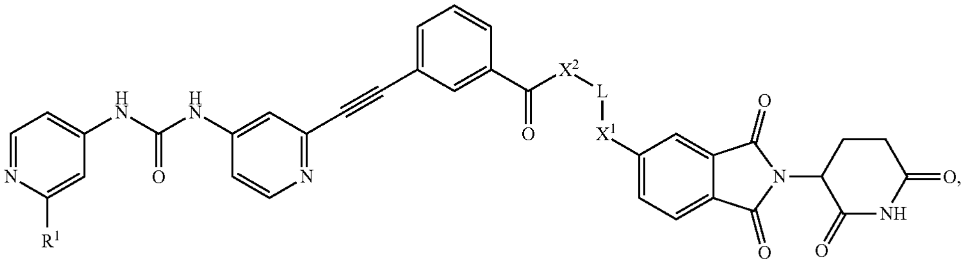
,

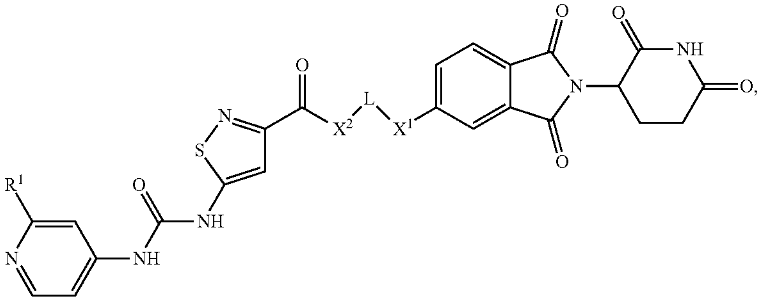
,

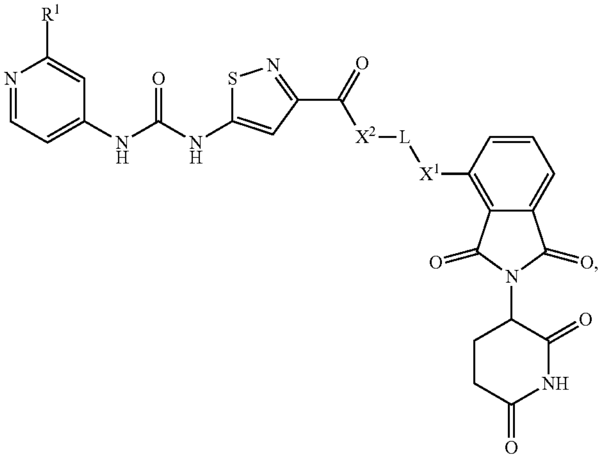
,

-continued
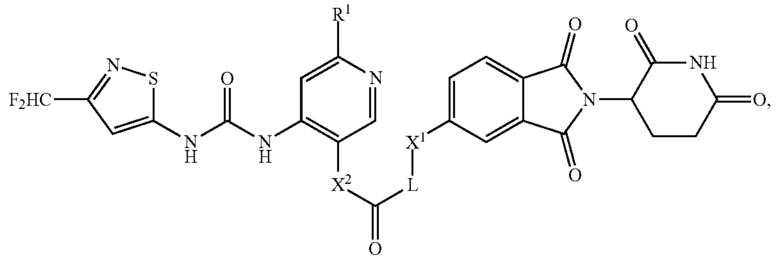
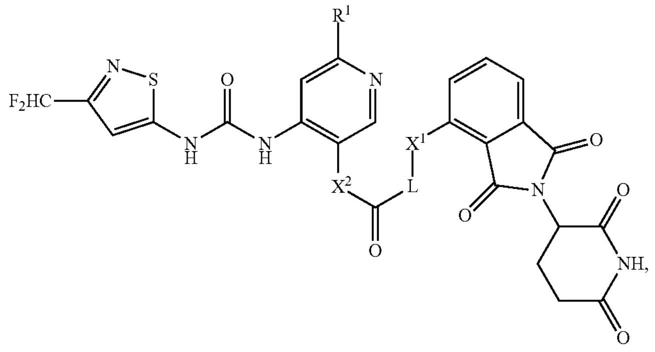
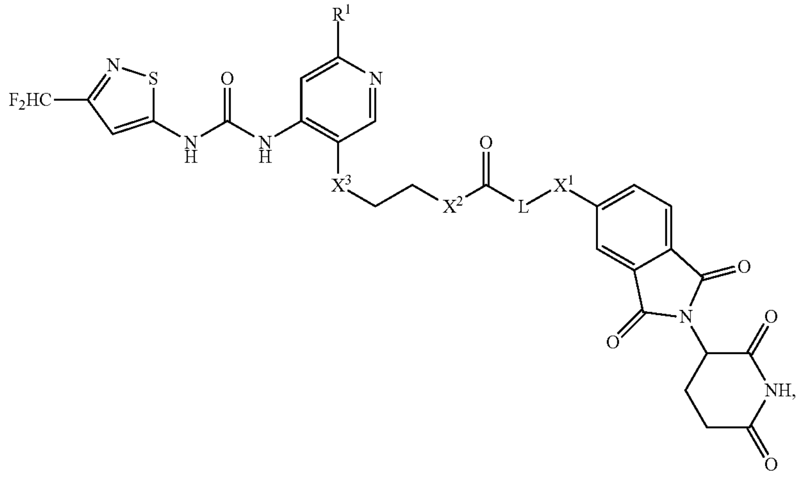
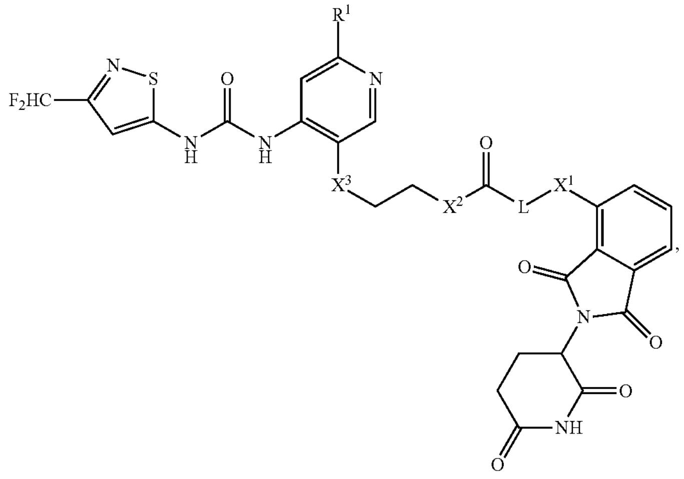

-continued
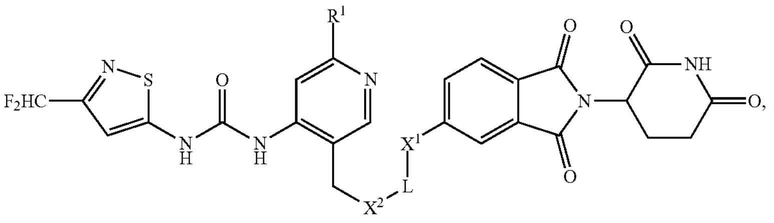
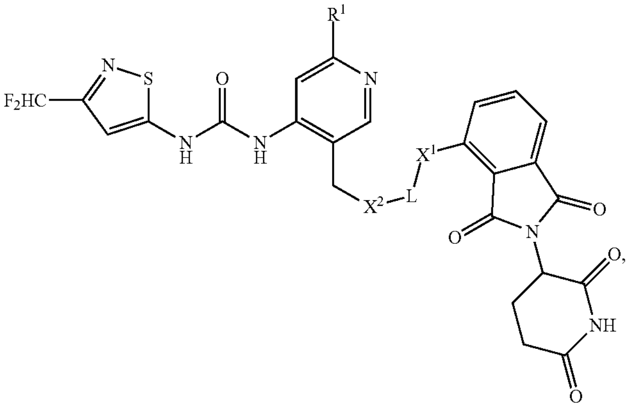
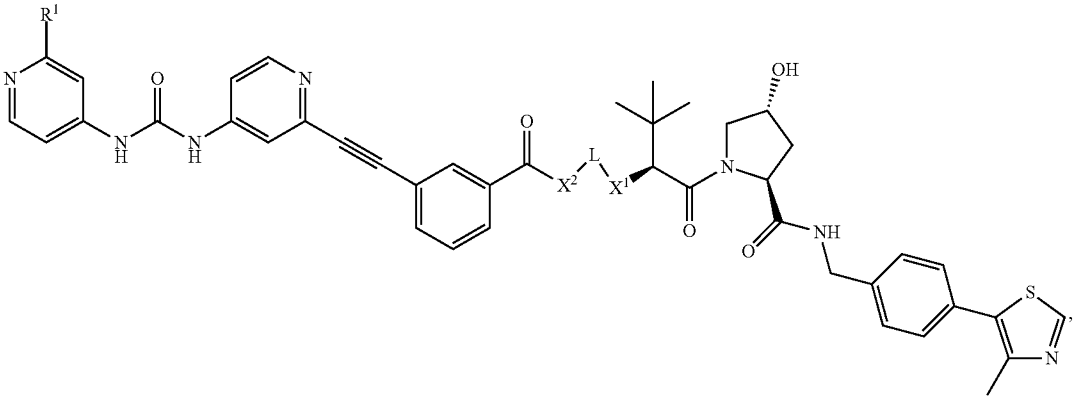
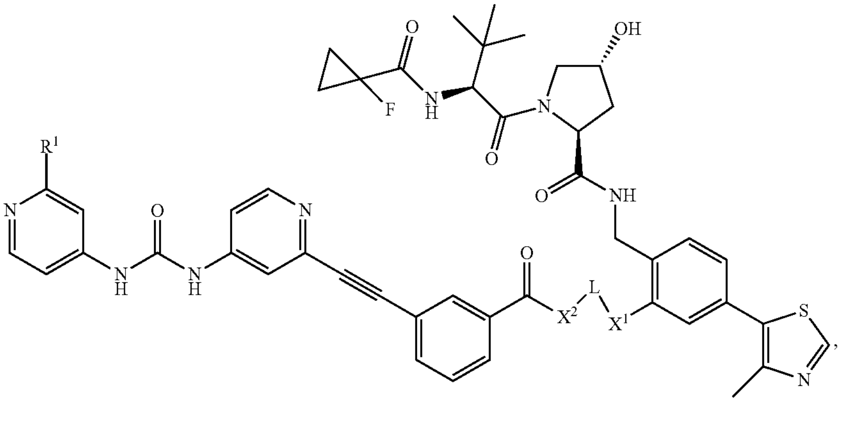

-continued
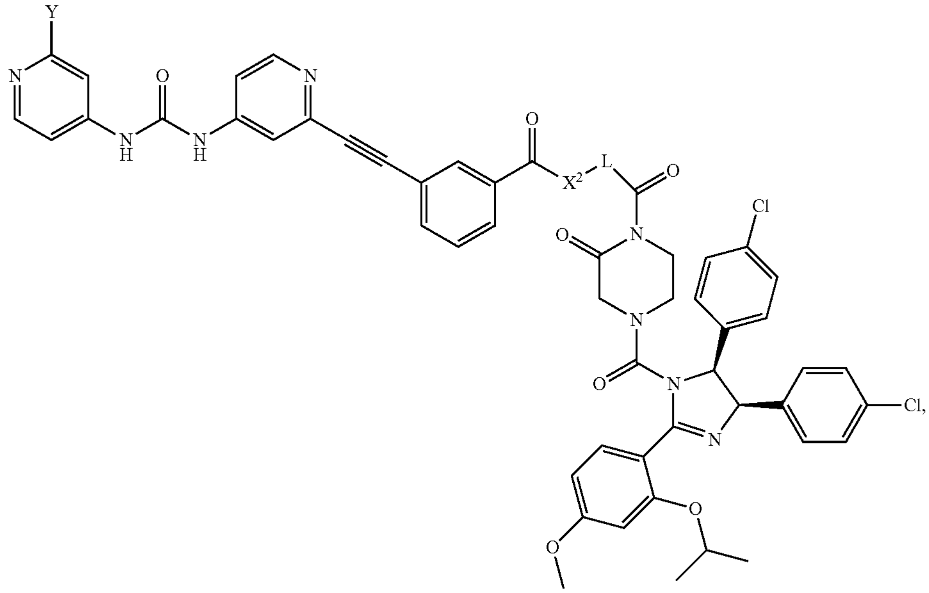
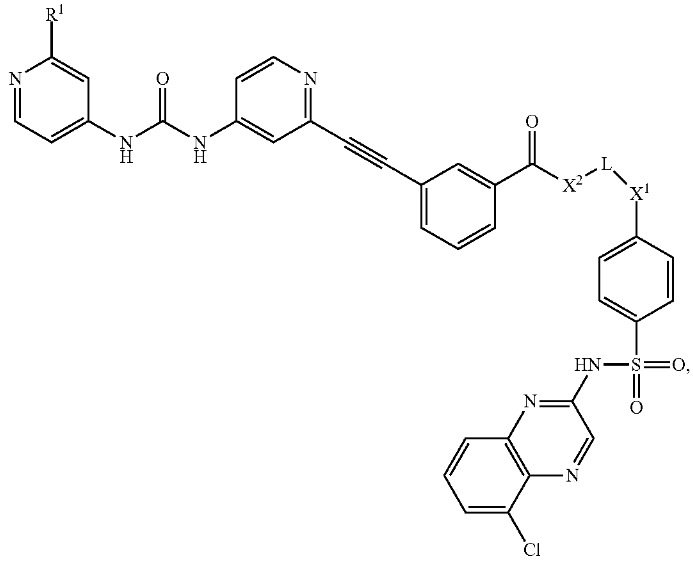
or
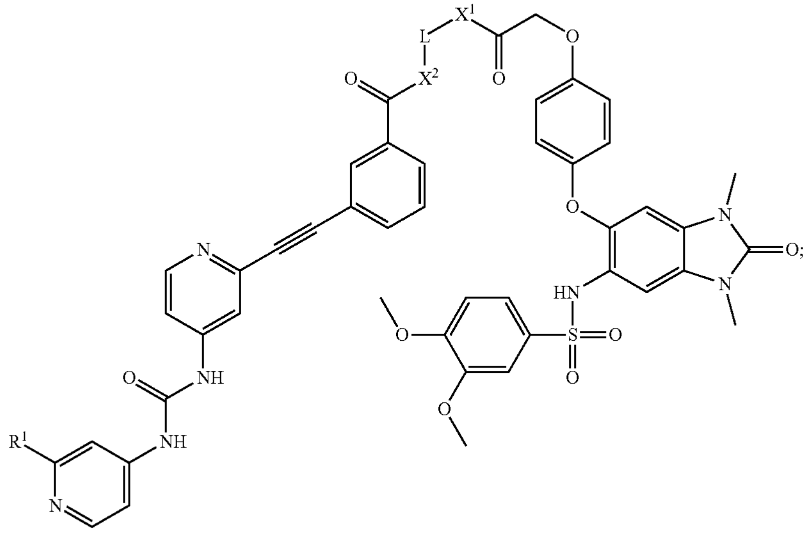

or a pharmaceutically acceptable salt thereof.

In certain embodiments of formula I, $X^1$ is NH. In other embodiments $X^1$.

In certain embodiments of formula I, $X^3$ is NH. In other embodiments $X^3$.

In certain embodiments of formula I, $X^2$ is NH. In other embodiments $X^2$. In yet other embodiments, $X^2$ combines with L to form a heterocyclyl (e.g., piperidinyl).

In certain embodiments of formula I, L is cycloalkylene (e.g., cyclohexyl). In other embodiments, L is alkylene. In certain embodiments, the alkylene comprises 2-25 carbon atoms. In certain embodiments, the alkylene comprises 2 carbon atoms. In other embodiments, the alkylene comprises 3 carbon atoms. In yet other embodiments, the alkylene comprises 4 carbon atoms. In yet other embodiments, the alkylene comprises 5 carbon atoms. In yet other embodiments, the alkylene comprises 6 carbon atoms. In yet other embodiments, the alkylene comprises 7 carbon atoms. In yet other embodiments, the alkylene comprises 8 carbon atoms. In yet other embodiments, the alkylene comprises 9 carbon atoms. In yet other embodiments, the alkylene comprises 10 carbon atoms. In yet other embodiments, the alkylene comprises 11 carbon atoms. In yet other embodiments, the alkylene comprises 12 carbon atoms. In yet other embodiments, the alkylene comprises 13 carbon atoms. In yet other embodiments, the alkylene comprises 14 carbon atoms. In yet other embodiments, the alkylene comprises 15 carbon atoms. In yet other embodiments, the alkylene comprises 16 carbon atoms. In yet other embodiments, the alkylene comprises 17 carbon atoms. In yet other embodiments, the alkylene comprises 18 carbon atoms. In yet other embodiments, the alkylene comprises 19 carbon atoms. In yet other embodiments, the alkylene comprises 20 carbon atoms. In yet other embodiments, the alkylene comprises 21 carbon atoms. In yet other embodiments, the alkylene comprises 22 carbon atoms. In yet other embodiments, the alkylene comprises 23 carbon atoms. In yet other embodiments, the alkylene comprises 24 carbon atoms. In yet other embodiments, the alkylene comprises 25 carbon atoms. In certain embodiments, at least one, but no more than five, methylene moieties of the alkylene are replaced with an amide moiety (e.g., 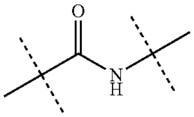 ).

In certain embodiments, at least one methylene moiety of the alkylene is replaced with an amide moiety (e.g., 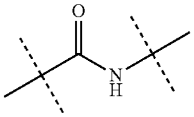 ).

In certain embodiments, at least two methylene moieties of the alkylene are replaced with two amide moieties (e.g., 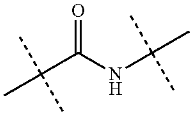 ).

In certain embodiments, at least three methylene moieties of the alkylene are replaced with three amide moieties (e.g., 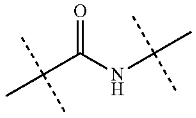 ).

In certain embodiments, one, two, three, or six methylene moieties of the alkylene are replaced with one, two, three, or six amide moieties (e.g., 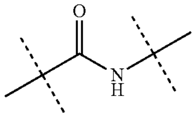 ).

In certain embodiments, the amide moieties are not adjacent. In certain embodiments, the amide moieties are separated by at least one carbon atom. In certain embodiments, the amide moieties are separated by at least six carbon atoms. In certain embodiments, at least one, but no more than ten, methylene moieties of the alkylene is replaced by an oxygen atom. In certain embodiments, at least one methylene moiety of the alkylene is replaced by an oxygen atom. In certain embodiments, at least two methylene moieties of the alkylene are replaced by at least two oxygen atoms. In certain embodiments, at least six methylene moieties of the alkylene are replaced by at least six oxygen atoms. In certain embodiments, one, two, or six methylene moieties of the alkylene are replaced by oxygen atom(s).

In certain preferred embodiments of formula I, n is 1.

In certain embodiments, the compound of formula I is selected from:

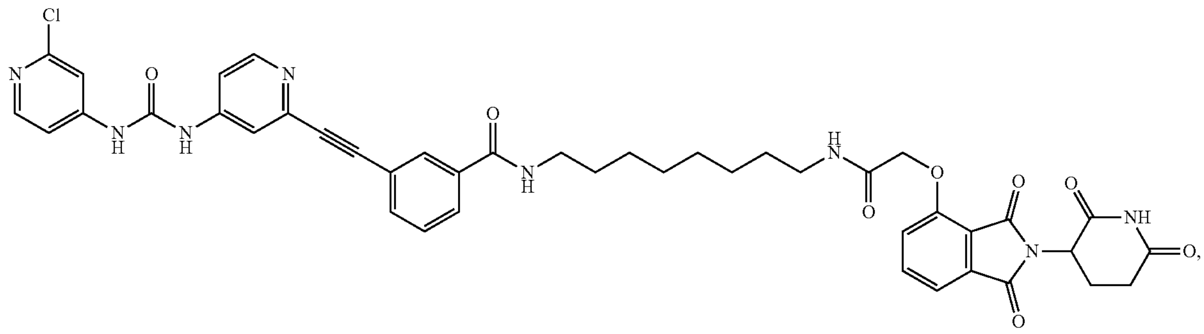,

-continued
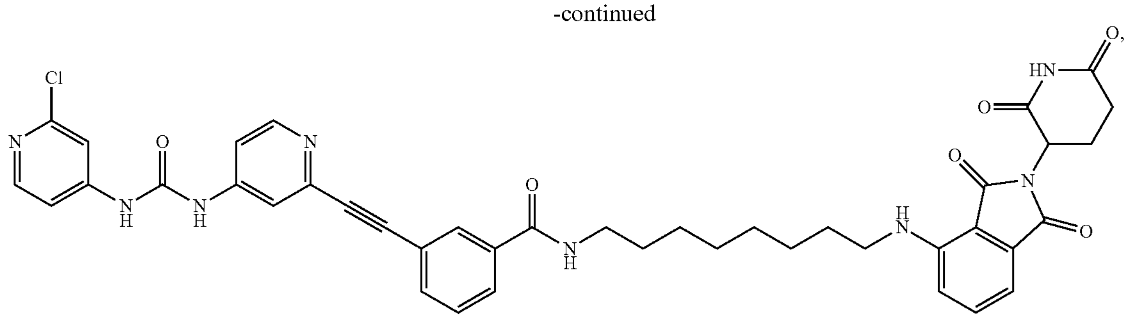
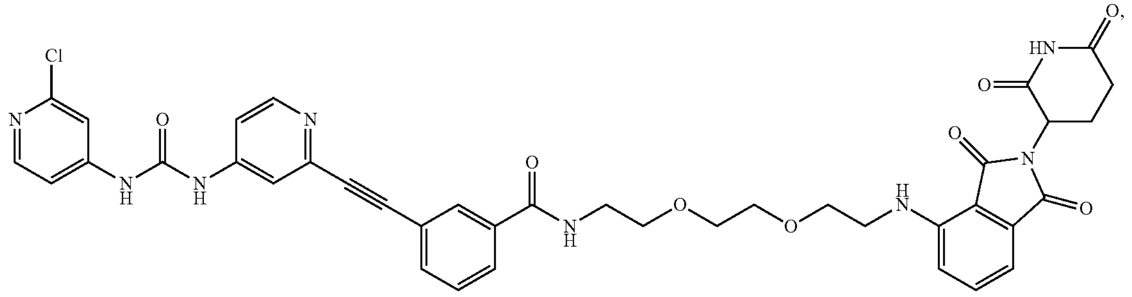
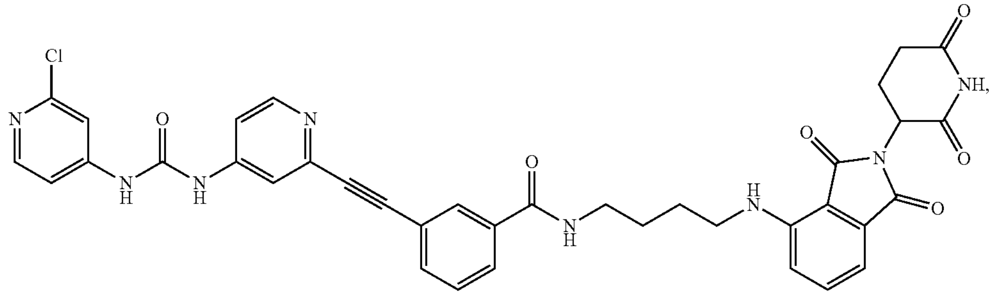
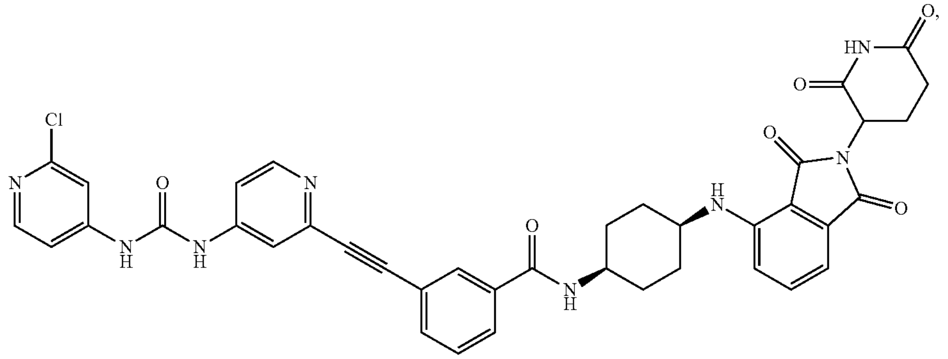
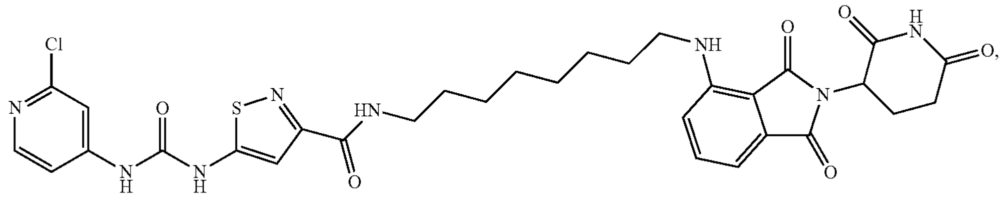
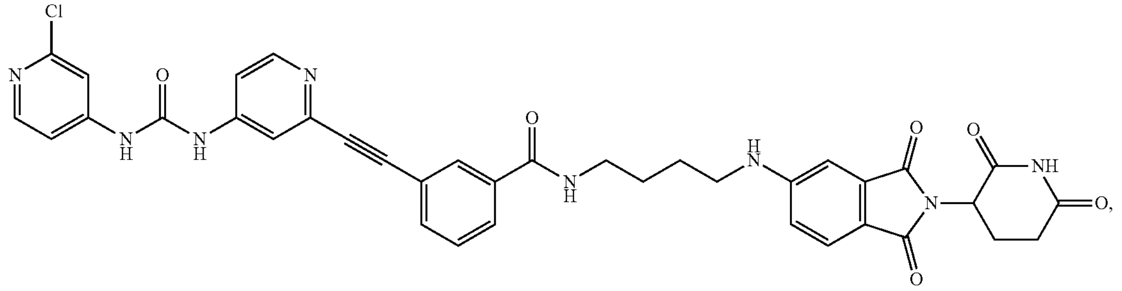

-continued
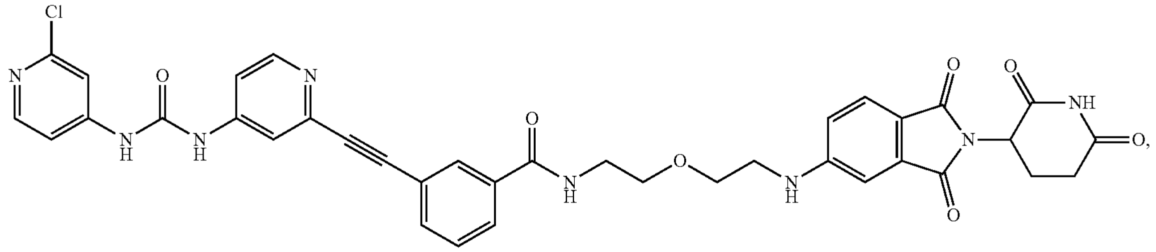
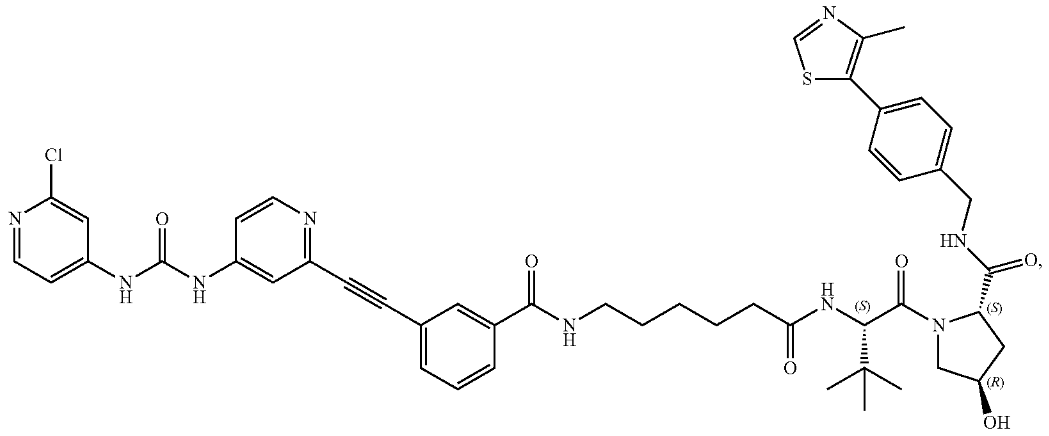
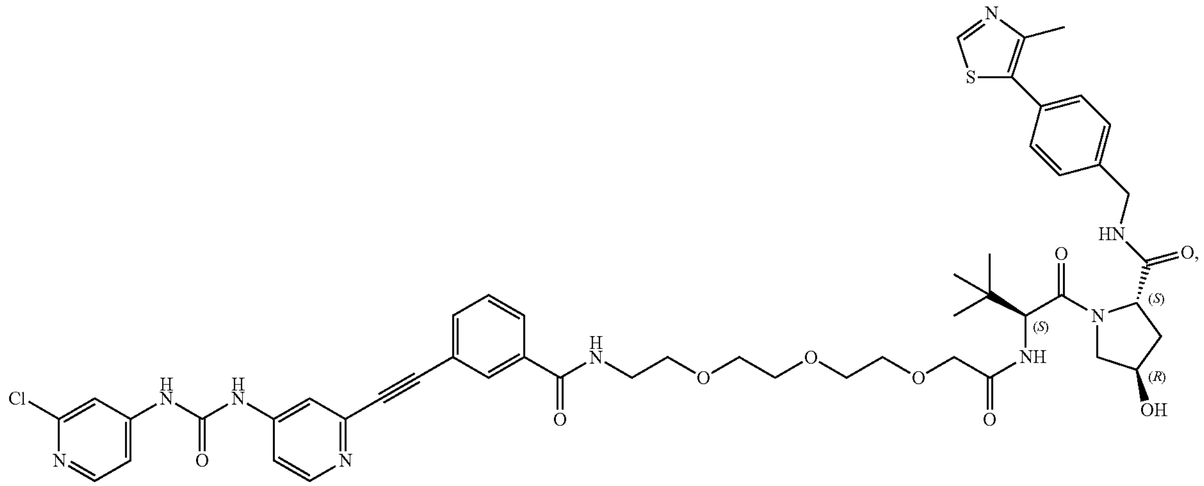
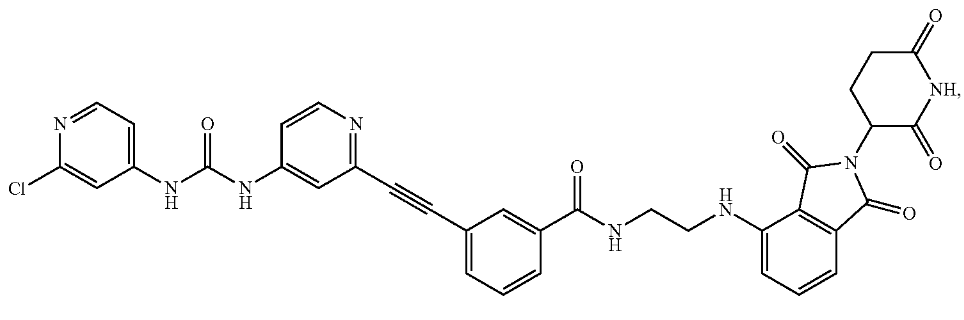

-continued

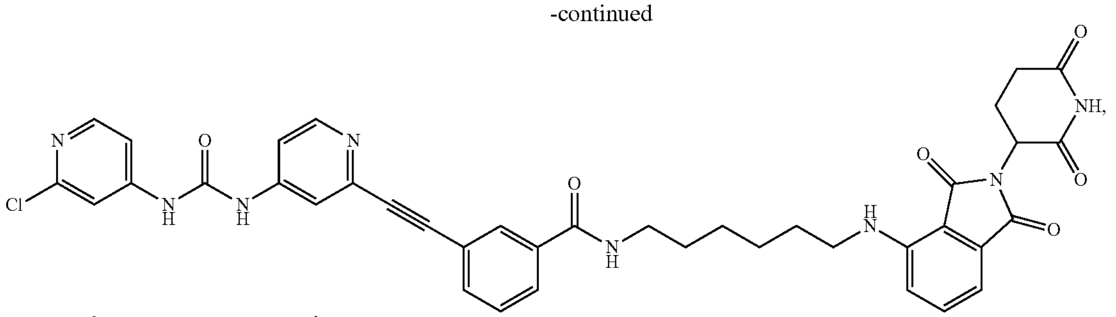

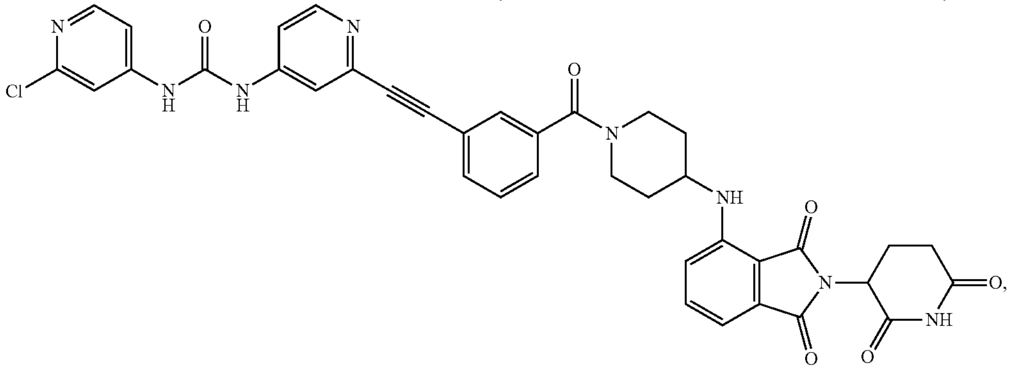

and

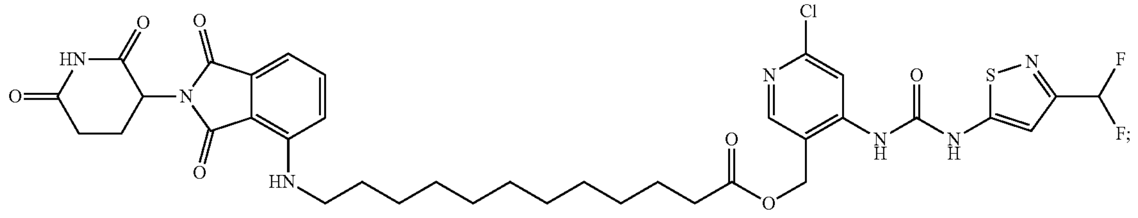

or a pharmaceutically acceptable salt thereof.

Exemplary Methods of the Disclosure

In one aspect, the disclosure provides a method of degrading SMARCA2, SMARCA4, or BRM, comprising contacting a cell with a compound of the disclosure or a pharmaceutically acceptable salt thereof. In certain embodiments, the amount of the compound used is an effective amount.

In another aspect, the disclosure provides a method of treating a disease or disorder, comprising administering to a subject in need thereof a compound of the disclosure. In certain embodiments, the amount of the compound used is a therapeutically effective amount.

In yet another aspect, the disclosure provides a method of treating a disease or disorder that benefits from degradation of SMARCA2, SMARCA4, or BRM, comprising administering to a subject in need thereof a compound of the disclosure. In certain embodiments, the amount of the compound used is a therapeutically effective amount.

In certain embodiments of the methods described herein, the disease or disorder benefits from the degradation of SMARCA2.

In certain embodiments of the methods described herein, the disease or disorder benefits from the degradation of SMARCA4.

In certain embodiments of the methods described herein, the disease or disorder benefits from the degradation of BRM.

In certain embodiments of the methods described herein, the disease or disorder is cancer. In certain embodiments, the cancer is selected from synovial sarcoma, lung cancer, ovarian cancer, brain cancer, kidney cancer, leukemia, non-small cell lung cancer, Burkitt's Lymphoma, childhood medulloblastoma, pancreatic adenocarcinoma, ovarian clear cell carcinoma, renal cell carcinoma, endometrial carcinomas and melanoma.

In certain embodiments of the methods described herein, the method further comprises conjointly administering one or more additional chemotherapeutic agents.

Pharmaceutical Compositions

The compositions and methods of embodiments of the invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

In some embodiments, the disclosure includes the use of pharmaceutically acceptable salts of compounds of the invention in the compositions and methods of the invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, l-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques described herein are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds described herein can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

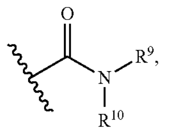

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

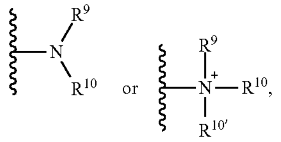

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

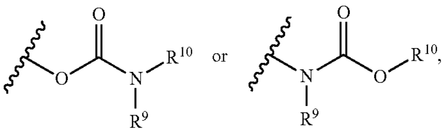

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —$OSO_3H$, or a pharmaceutically acceptable salt thereof.

The term "sulfonamide" is art-recognized and refers to the group represented by the general formulae

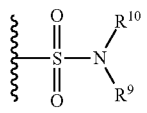

or

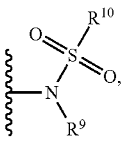

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group $SO_3H$, or a pharmaceutically acceptable salt thereof.

The term "sulfone" is art-recognized and refers to the group —$S(O)_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —$C(O)SR^9$ or —$SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

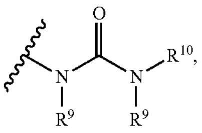

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form a compound described herein (e.g., compounds of formula I). Typical examples of prodrugs include compounds that have biologically labile or cleavable (protecting) groups on a functional moiety of the active compound.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the invention, and are not intended to limit the invention.

Example A—Preparation of Exemplary Compounds

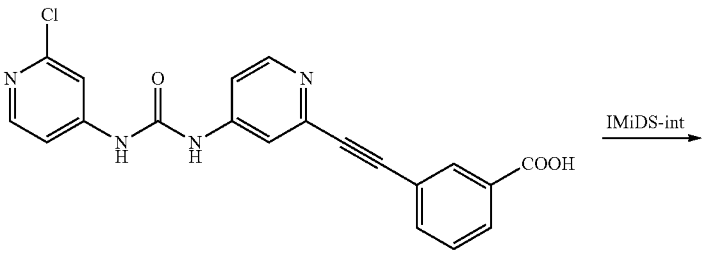

Int1

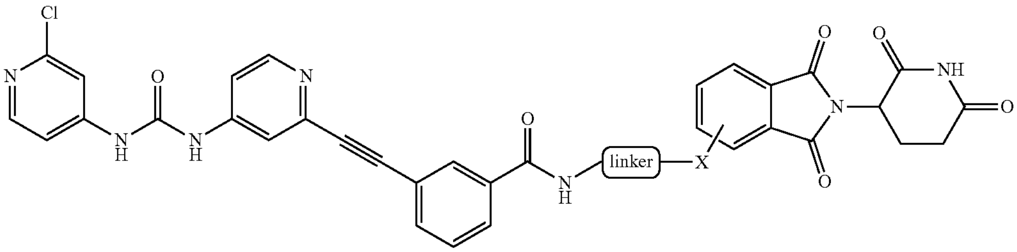

Exp. 1-5

Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. In certain embodiments, the disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

General Procedure A

To a 8 mL flask fitted with a stir bar was added Int1 (10 mg, 0.025 mmol, 1 eq.) and HATU (19 mg, 0.05 mmol, 2 eq.). Then DMF (1 mL) was added to generate a colorless solution, then DIPEA (8.3 μL, 2 eq.) was added and the resulting mixture was stirred at room temperature for 5 min. After that, IMiDs-int (0.028 mmol, 1.1 eq.) was added into the reaction flask. The reaction was continue stirred at room temperature for 4 hours. After that, the reaction mixture was worked-up by adding 5 mL water, then extracted with ethyl acetate (2 mL×3). The organic layers were combined and dried over $Na_2SO_4$, then concentrated to get the residue. The residue was purified via ISCO (Methanol/Methylene chloride=0~10%) to give example compound Example 1
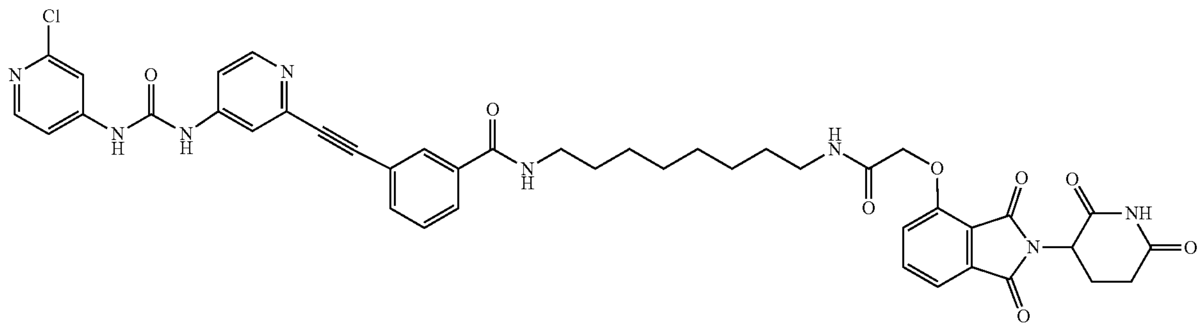 [SMILES: O=C(COc1cccc2c1C(=O)N(C1CCC(=O)NC1=O)C2=O)NCCCCCCCCNC(=O)c1cccc(C#Cc2cc(NC(=O)Nc3ccnc(Cl)c3)ccn2)c1]
According to general procedure A, Light yellow powder was obtained, 1.2 mg, yield: 6.0%. MS (ESI) calcd. For: C43H41ClN8O8: 832.27, Found: [M+1]833.34, 834.29.
Example 2
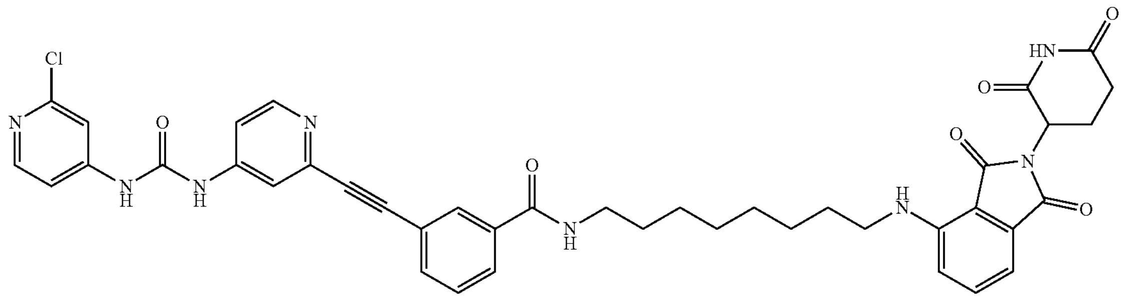 [SMILES: O=C1CCC(N2C(=O)c3cccc(NCCCCCCCCNC(=O)c4cccc(C#Cc5cc(NC(=O)Nc6ccnc(Cl)c6)ccn5)c4)c3C2=O)C(=O)N1]
According to general procedure A, Yellow powder, 5 mg, yield: 26%. MS (ESI) calcd. for C41H39ClN8O6: 774.27, Found: [M+1]775.54, 777.14. $^1$H NMR (500 MHz, Acetone-$d_6$) δ 9.76 (s, 1H), 9.44 (d, J=17.2 Hz, 1H), 8.33 (d, J=5.7 Hz, 1H), 8.07 (d, J=5.6 Hz, 1H), 7.96 (d, J=1.8 Hz, 1H), 7.86-7.74 (m, 3H), 7.66-7.58 (m, 2H), 7.48-7.37 (m, 3H), 7.30 (dd, J=5.6, 2.0 Hz, 1H), 6.95 (d, J=8.6 Hz, 1H), 6.88 (d, J=7.0 Hz, 1H), 6.27 (d, J=6.6 Hz, 1H), 4.96-4.91 (m, 1H), 3.30 (td, J=7.1, 5.6 Hz, 2H), 3.25-3.23 (m, 2H), 2.84-2.79 (m, 2H), 2.69-2.61 (m, 4H), 2.07 (dddd, J=16.5, 6.2, 5.2, 2.8 Hz, 2H), 1.54 (dq, J=24.4, 7.1 Hz, 6H), 1.32 (s, 2H).
Example 3
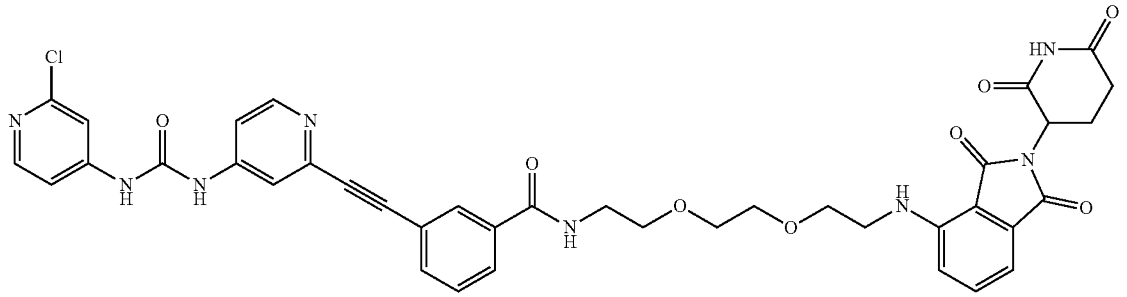

According to general procedure A, Yellow powder, 6.5 mg, yield: 33%. MS (ESI) calcd. for C39H35ClN8O8: 778.23, Found: [M+1]779.34, 780.29, 782.31. $^1$H NMR (500 MHz, Acetone-$d_6$) δ 9.95 (s, 1H), 9.09 (s, 1H), 9.00 (s, 1H), 8.45 (d, J=5.6 Hz, 1H), 8.22 (d, J=5.6 Hz, 1H), 8.08 (d, J=1.9 Hz, 1H), 7.95 (d, J=7.8 Hz, 1H), 7.87 (dd, J=23.4, 4.0 Hz, 2H), 7.76 (d, J=1.9 Hz, 1H), 7.71 (d, J=7.6 Hz, 1H), 7.53 (dt, J=18.9, 7.8 Hz, 2H), 7.45 (ddd, J=14.4, 5.6, 2.1 Hz, 2H), 7.08 (d, J=8.5 Hz, 1H), 7.02 (d, J=7.0 Hz, 1H), 6.61 (t, J=5.7 Hz, 1H), 5.08 (dd, J=12.4, 5.4 Hz, 1H), 3.78 (t, J=5.3 Hz, 2H), 3.71 (d, J=5.8 Hz, 2H), 3.62 (t, J=5.5 Hz, 2H), 3.53 (d, J=5.2 Hz, 2H), 2.96 (ddt, J=18.9, 14.8, 4.4 Hz, 2H), 2.79-2.75 (m, 2H), 2.21 (ddt, J=13.3, 7.8, 3.8 Hz, 2H), 1.52 (d, J=6.6 Hz, 2H).

Example 4

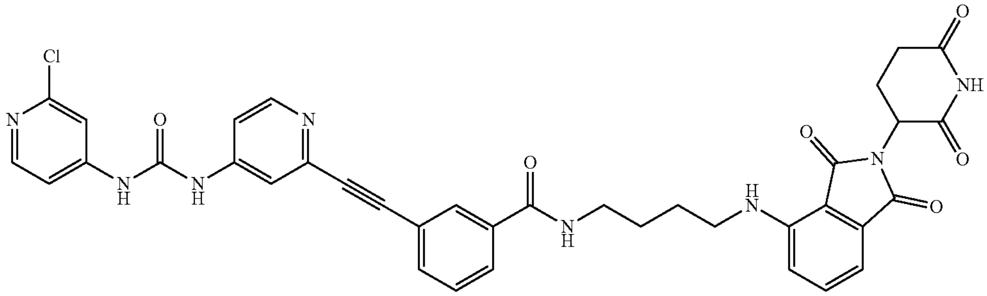 [SMILES: O=C1CCC(N2C(=O)c3cccc(NCCCCNC(=O)c4cccc(C#Cc5cc(NC(=O)Nc6ccnc(Cl)c6)ccn5)c4)c3C2=O)C(=O)N1]

According to general procedure A, Yellow powder, 4.2 mg, yield: 24%. MS (ESI) calcd. for C37H31ClN8O6: 718.21, Found: [M+1]719.34, 721.32. $^1$H NMR (500 MHz, Acetone-$d_6$) δ 9.76 (s, 1H), 9.12 (d, J=9.7 Hz, 1H), 9.07 (s, 1H), 8.33 (d, J=5.7 Hz, 1H), 8.08 (d, J=5.6 Hz, 1H), 7.96 (d, J=1.8 Hz, 1H), 7.90-7.75 (m, 3H), 7.64-7.58 (m, 2H), 7.42 (dt, J=17.7, 7.5 Hz, 2H), 7.36 (dd, J=5.6, 2.1 Hz, 1H), 7.30 (dd, J=5.7, 1.9 Hz, 1H), 6.99 (d, J=8.6 Hz, 1H), 6.88 (d, J=7.1 Hz, 1H), 6.32 (d, J=6.0 Hz, 1H), 4.93 (dd, J=12.6, 5.4 Hz, 1H), 3.39 (q, J=6.1 Hz, 2H), 3.35-3.30 (m, 2H), 2.82 (q, J=2.9, 2.3 Hz, 2H), 2.66-2.59 (m, 2H), 2.09-2.03 (m, 1H), 1.74-1.62 (m, 4H).

Example 5

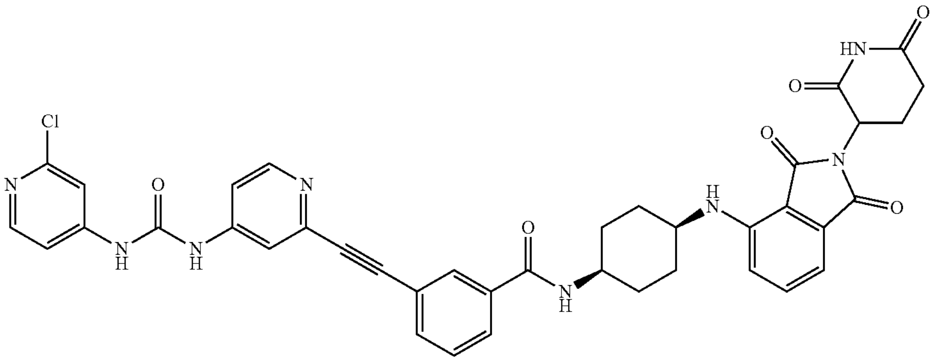 [SMILES: O=C1CCC(N2C(=O)c3cccc(N[C@H]4CC[C@@H](NC(=O)c5cccc(C#Cc6cc(NC(=O)Nc7ccnc(Cl)c7)ccn6)c5)CC4)c3C2=O)C(=O)N1]

According to general procedure A, Yellow powder, 2.76 mg, yield: 15%. MS (ESI) calcd. for C39H33ClN8O6: 744.22, Found: [M+1]745.41, 747.38.

Example 6

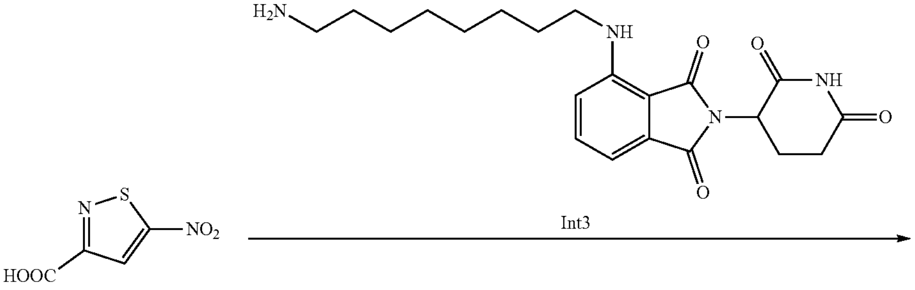

Int2

-continued

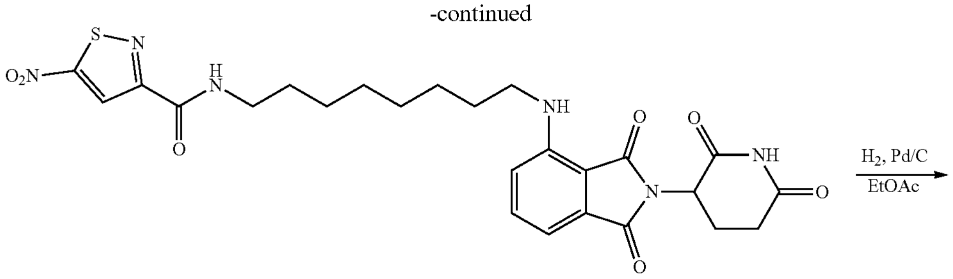

Int4

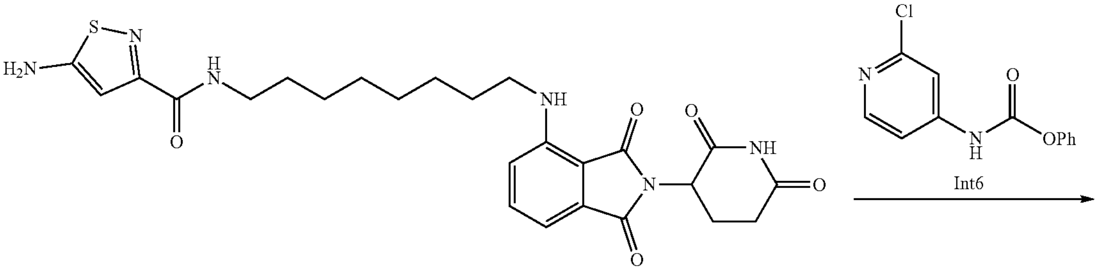

Int5

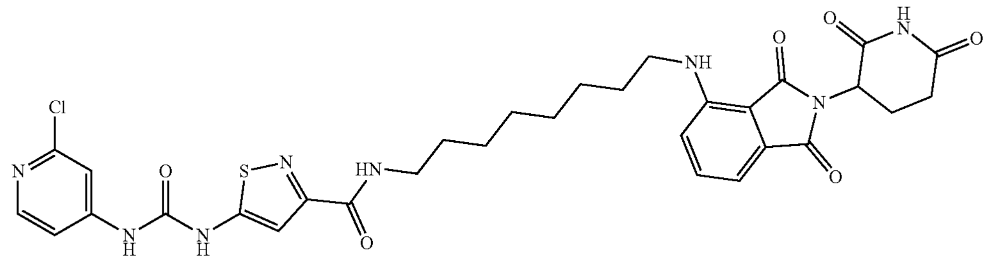

Example 6

According to general procedure A, Int4 was obtained as yellow gel, 90 mg, yield: >99%. MS (ESI) calcd. for Chemical Formula: C25H28N6O7S: 556.17, Found: [M+1] 557.27, 558.34.

To a 50 mL round-bottom flask were added Int4 (90 mg) and dissolved by EtOAc (3 mL) to get a solution. Then Pd/C (18 mg, 20 wt %) was added and the result reaction mixture was purged with H2 for 3 times and then allowed to stir at room temperature for 16 minutes. After that, Pd/C was removed by filtration and the solvent get removed under reduced pressure to get the Int5 80 mg, yield: 94%. MS (ESI) calcd. for Chemical Formula: C25H30N6O5S: 526.20, Found: [M+OH]543.33, 544.35. $^{1}$H NMR (500 MHz, Chloroform-d) δ 7.95 (s, 2H), 7.58-7.38 (m, 2H), 7.18-7.12 (m, 1H), 7.05-6.97 (m, 2ldyH), 6.84-6.78 (m, 1H), 6.16 (d, J=5.9 Hz, 1H), 4.90-4.80 (m, 1H), 3.43-3.28 (m, 2H), 3.22-3.13 (m, 2H), 2.79 (d, J=7.8 Hz, 2H), 2.73-2.64 (m, 2H), 2.11-1.92 (m, 2H), 1.55 (d, J=26.1 Hz, 4H), 1.30 (d, J=13.7 Hz, 6H).

To a 8 mL flask fitted with a stir bar was added Int5 (8 mg, 0.015 mmol, 1 eq.), Int6 (4.1 mg, 0.017 mmol, 1.1 eq.), dissolved by DMF (2 mL) to get a solution. Then LiHMDS (30 μL, 1 M, 2 eq.) was added and the result reaction mixture was allowed to stir at room temperature for 1 hour. After that, 1 mL of MeOH was added to quench the reaction and the mixture was purified by HPLC (water/acetonitrile=95%~5%) to get the Example 6 1.2 mg, yield: 12%. MS (ESI) calcd. for Chemical Formula: C31H33ClN8O6S: 680.19, Found: [M+1]681.46, [M+OH]697.34, 699.35.

Example 7

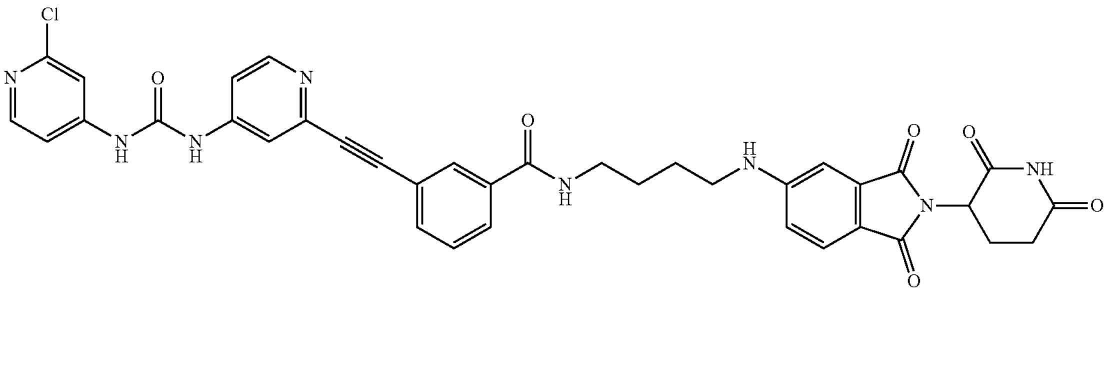 [SMILES: O=C1CCC(N2C(=O)c3ccc(NCCCCNC(=O)c4cccc(C#Cc5cc(NC(=O)Nc6ccnc(Cl)c6)ccn5)c4)cc3C2=O)C(=O)N1]

According to general procedure A, Yellow powder, 7.4 mg, yield: 50%. MS (ESI) calcd. for C37H31ClN8O6: 718.21, Found: [M+1]719.46, 721.47. 1H NMR (500 MHz, Acetone-d6) δ 9.72 (s, 1H), 9.12 (s, 1H), 9.04 (s, 1H), 8.31 (d, J=5.6 Hz, 1H), 8.07 (d, J=5.6 Hz, 1H), 7.95 (t, J=1.7 Hz, 1H), 7.88 (ddd, J=7.6, 3.1, 1.7 Hz, 1H), 7.82 (dt, J=7.9, 1.5 Hz, 1H), 7.77 (d, J=2.1 Hz, 1H), 7.63-7.58 (m, 2H), 7.41 (dd, J=8.1, 2.5 Hz, 2H), 7.35 (dt, J=5.9, 1.7 Hz, 1H), 7.30 (dd, J=5.7, 2.0 Hz, 1H), 6.88 (d, J=2.2 Hz, 1H), 6.80 (dd, J=8.4, 2.2 Hz, 1H), 6.28 (t, J=5.4 Hz, 1H), 4.90 (dd, J=12.6, 5.4 Hz, 1H), 3.38 (q, J=6.1 Hz, 2H), 3.27-3.19 (m, 2H), 2.82 (q, J=3.1 Hz, 2H), 2.66-2.61 (m, 2H), 2.06-2.01 (m, 1H), 1.68 (h, J=3.0 Hz, 4H).

Example 8

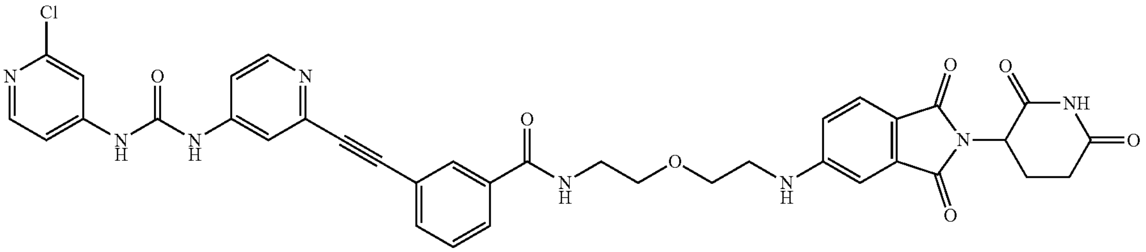 [SMILES: O=C1CCC(N2C(=O)c3ccc(NCCOCCNC(=O)c4cccc(C#Cc5cc(NC(=O)Nc6ccnc(Cl)c6)ccn5)c4)cc3C2=O)C(=O)N1]

According to general procedure A, Yellow powder, 8.1 mg, yield: 54%. MS (ESI) calcd. for C37H31ClN8O7: 734.20, Found: [M+1]735.45, 736.44, 738.42. 1H NMR (500 MHz, Acetone-d6) δ 9.93 (s, 1H), 9.33 (d, J=7.8 Hz, 1H), 9.26 (s, 1H), 8.47-8.41 (m, 2H), 8.21 (d, J=5.6 Hz, 1H), 8.11 (t, J=1.8 Hz, 1H), 7.95 (dt, J=7.9, 1.4 Hz, 1H), 7.90 (d, J=2.1 Hz, 1H), 7.77 (d, J=1.9 Hz, 1H), 7.76-7.71 (m, 1H), 7.57-7.51 (m, 3H), 7.45 (dd, J=5.6, 2.0 Hz, 1H), 7.14 (dd, J=8.6, 2.2 Hz, 1H), 7.02 (dd, J=6.9, 1.2 Hz, 1H), 6.64 (s, 1H), 5.04 (dd, J=12.7, 5.5 Hz, 1H), 3.80 (t, J=5.3 Hz, 2H), 3.75 (t, J=5.6 Hz, 2H), 3.66 (q, J=5.5 Hz, 2H), 3.59-3.55 (m, 2H), 2.99-2.93 (m, 2H), 2.80-2.75 (m, 2H), 2.19 (tdd, J=9.3, 3.3, 1.8 Hz, 2H).

Example 9

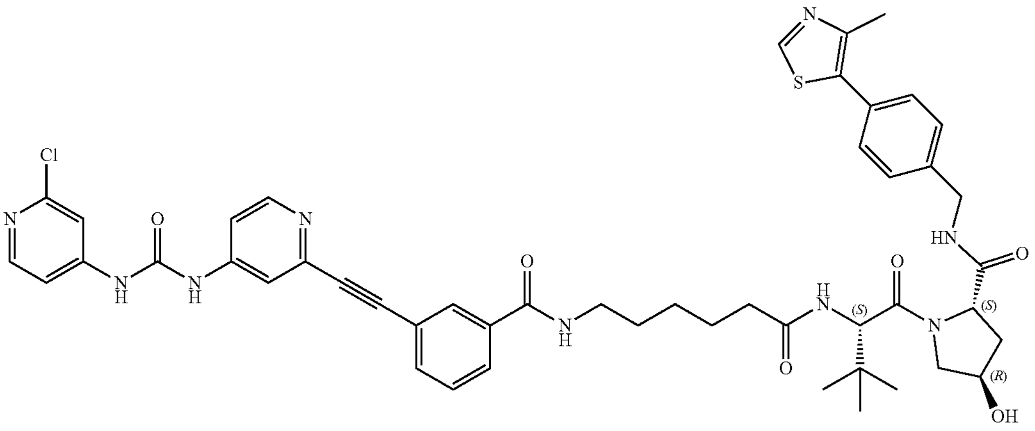

According to general procedure A, white powder, 10 mg, yield: 39%. MS (ESI) calcd. for C48H52ClN9O6S: 917.34, Found: [M+1]918.35. $^1$H NMR (500 MHz, Acetone-$d_6$) δ 9.52 (s, 1H), 9.47 (s, 1H), 8.85 (s, 1H), 8.45 (d, J=5.7 Hz, 1H), 8.21 (d, J=5.6 Hz, 1H), 8.11-8.10 (m, 1H), 8.02 (q, J=6.1 Hz, 1H), 7.96 (dt, J=8.1, 1.3 Hz, 1H), 7.80 (d, J=2.1 Hz, 1H), 7.76 (d, J=1.9 Hz, 1H), 7.74-7.71 (m, 1H), 7.61-7.57 (m, 1H), 7.53 (t, J=7.8 Hz, 1H), 7.47 (d, J=1.6 Hz, 1H), 7.46 (d, J=2.0 Hz, 1H), 7.42 (d, J=6.3 Hz, 3H), 7.40 (d, J=2.5 Hz, 1H), 4.72 (dd, J=9.6, 7.5 Hz, 2H), 4.61-4.53 (m, 2H), 4.39 (dd, J=15.4, 5.5 Hz, 1H), 4.03 (d, J=15.5 Hz, 1H), 3.95 (d, J=15.5 Hz, 1H), 3.91-3.85 (m, 1H), 3.82 (dd, J=10.7, 4.0 Hz, 1H), 3.68-3.64 (m, 9H), 2.47 (s, 3H), 2.21 (dd, J=5.2, 3.3 Hz, 1H), 1.03 (s, 9H).

Example 10

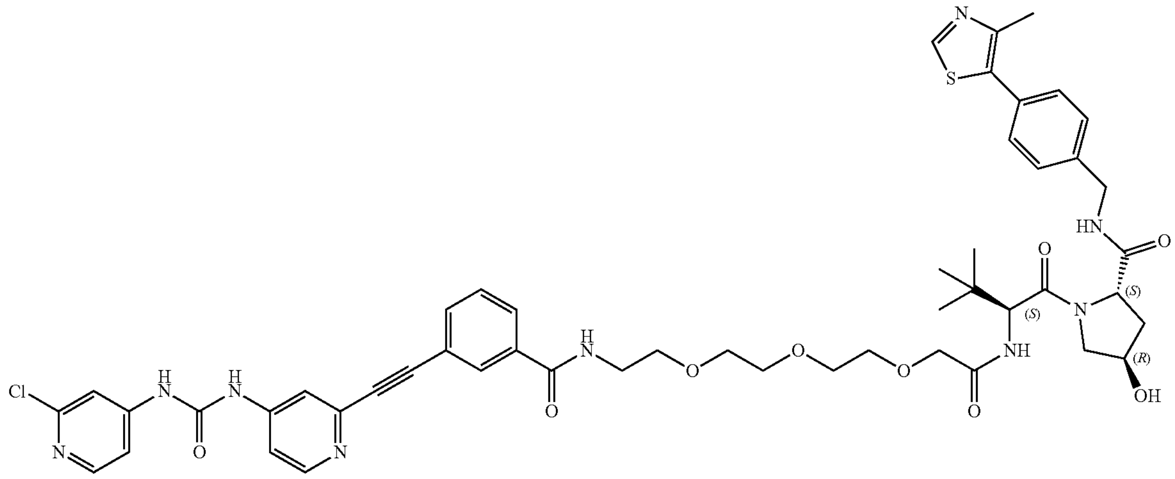

According to general procedure A, Yellow powder, 12 mg, yield: 47%. MS (ESI) calcd. for C50H56ClN9O9S: 993.36, Found: [M+1]994.69. $^1$H NMR (500 MHz, Acetone-$d_6$) δ 11.67 (s, 1H), 11.55 (s, 1H), 8.80 (s, 1H), 8.35 (d, J=5.7 Hz, 1H), 8.11 (dd, J=5.5, 4.0 Hz, 1H), 8.06 (d, J=1.8 Hz, 1H), 7.97-7.88 (m, 3H), 7.82 (t, J=2.5 Hz, 1H), 7.69 (dt, J=7.7, 1.4 Hz, 1H), 7.60 (dd, J=5.6, 2.0 Hz, 1H), 7.52-7.46 (m, 2H), 7.44-7.39 (m, 2H), 7.38-7.33 (m, 2H), 7.05 (d, J=9.1 Hz, 1H), 4.62-4.44 (m, 5H), 4.36-4.25 (m, 2H), 3.87 (d, J=10.8 Hz, 1H), 3.70 (dd, J=10.7, 4.1 Hz, 1H), 3.65-3.58 (m, 1H), 3.39 (q, J=6.6 Hz, 2H), 3.30 (d, J=7.1 Hz, 1H), 3.07 (d, J=6.2 Hz, 2H), 2.42 (s, 3H), 2.25 (dt, J=12.0, 7.3 Hz, 4H), 2.13 (ddt, J=8.9, 3.1, 1.9 Hz, 2H), 0.94 (s, 9H).

Example 11

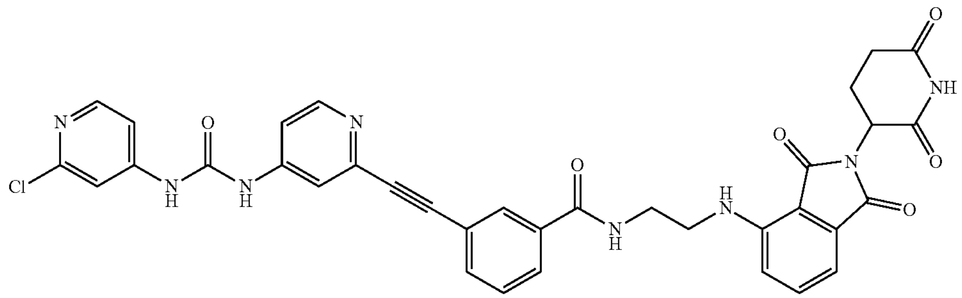 [SMILES: O=C1CCC(N2C(=O)c3cccc(NCCNC(=O)c4cccc(C#Cc5cc(NC(=O)Nc6ccnc(Cl)c6)ccn5)c4)c3C2=O)C(=O)N1]

According to general procedure A, Yellow powder, 3.2 mg, yield: 19%. MS (ESI) calcd. for C35H27ClN8O6: 690.17, Found: [M/2+1]346.40, [M+1]691.41. $^{1}$H NMR (500 MHz, Acetone-d6) δ 8.46 (d, J=5.6 Hz, 1H), 8.28 (s, 1H), 8.22 (d, J=5.6 Hz, 1H), 8.10 (d, J=1.8 Hz, 1H), 7.97 (dt, J=7.9, 1.5 Hz, 1H), 7.92 (dd, J=9.0, 2.1 Hz, 1H), 7.80-7.67 (m, 2H), 7.63-7.53 (m, 2H), 7.53-7.44 (m, 2H), 7.29 (d, J=8.5 Hz, 1H), 7.06 (d, J=7.0 Hz, 1H), 6.76 (d, J=6.4 Hz, 1H), 5.13-5.00 (m, 1H), 3.78-3.60 (m, 4H), 3.07-2.92 (m, 2H), 2.74 (dd, J=7.1, 3.3 Hz, 2H), 2.20 (ddd, J=6.9, 4.4, 2.1 Hz, 1H).

Example 12

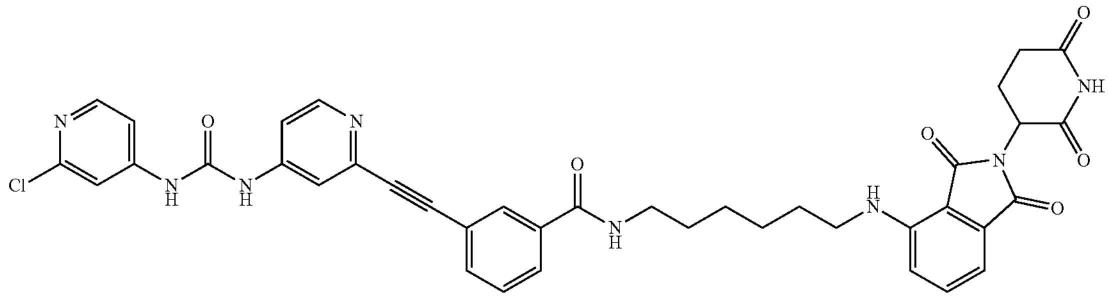 [SMILES: O=C1CCC(N2C(=O)c3cccc(NCCCCCCNC(=O)c4cccc(C#Cc5cc(NC(=O)Nc6ccnc(Cl)c6)ccn5)c4)c3C2=O)C(=O)N1]

According to general procedure A, Yellow powder, 20.2 mg, yield: 98%. MS (ESI) calcd. for C39H35ClN8O6: 746.24, Found: [M/2+1]374.44, [M+1]747.54. 1H NMR (500 MHz, Acetone-d6) δ 9.93 (s, 1H), 9.16 (d, J=37.6 Hz, 2H), 8.46 (d, J=5.6 Hz, 1H), 8.22 (d, J=5.6 Hz, 1H), 8.10 (t, J=1.8 Hz, 1H), 7.97 (dt, J=7.9, 1.5 Hz, 2H), 7.90 (d, J=2.1 Hz, 1H), 7.78-7.71 (m, 2H), 7.60-7.52 (m, 2H), 7.50-7.43 (m, 2H), 7.09 (d, J=8.5 Hz, 1H), 7.02 (d, J=7.1 Hz, 1H), 6.43 (t, J=5.8 Hz, 1H), 5.07 (dd, J=12.6, 5.5 Hz, 1H), 4.10-3.93 (m, 2H), 3.88-3.64 (m, 2H), 3.49-3.44 (m, 2H), 3.39 (td, J=6.3, 1.4 Hz, 2H), 2.97-2.94 (m, 2H), 2.80-2.75 (m, 2H), 2.25-2.18 (m, 1H), 1.71 (ddt, J=14.3, 7.2, 3.6 Hz, 4H).

Example 13

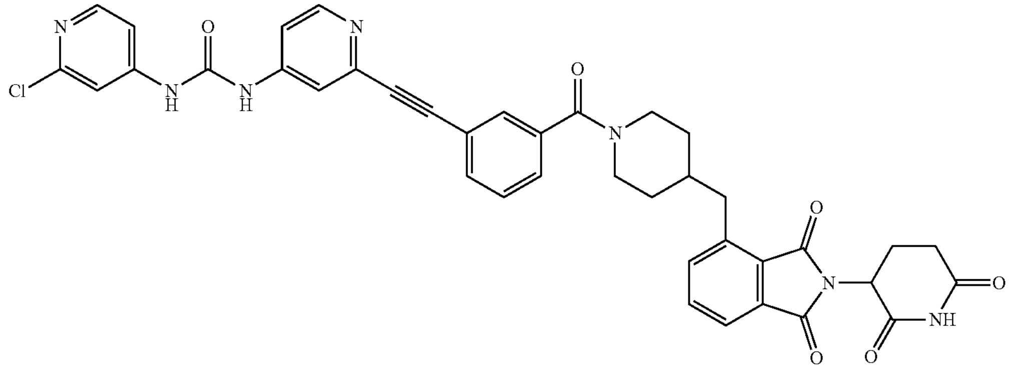 [SMILES: O=C1CCC(N2C(=O)c3cccc(CC4CCN(C(=O)c5cccc(C#Cc6cc(NC(=O)Nc7ccnc(Cl)c7)ccn6)c5)CC4)c3C2=O)C(=O)N1]

According to general procedure A, Yellow powder, 18.2 mg, yield: 97%. MS (ESI) calcd. for C38H31ClN8O6: 730.21, Found: [M+1]731.46, 732.41. 1H NMR (500 MHz, Acetone-d6) δ 9.93 (s, 1H), 9.15 (d, J=46.9 Hz, 2H), 8.45 (d, J=5.6 Hz, 1H), 8.22 (d, J=5.6 Hz, 1H), 7.87 (d, J=2.1 Hz, 1H), 7.75 (d, J=1.9 Hz, 1H), 7.73-7.67 (m, 2H), 7.61 (dd, J=8.6, 7.1 Hz, 1H), 7.55 (dd, J=4.7, 1.6 Hz, 2H), 7.50 (dd, J=5.6, 2.2 Hz, 1H), 7.44 (dd, J=5.6, 1.9 Hz, 1H), 7.25 (d, J=8.6 Hz, 1H), 7.07 (d, J=7.0 Hz, 1H), 6.38 (d, J=8.3 Hz, 1H), 5.14-5.01 (m, 1H), 4.60 (d, J=19.0 Hz, 1H), 4.04-3.94 (m, 1H), 3.78 (d, J=20.7 Hz, 1H), 3.33 (d, J=4.9 Hz, 2H), 3.01-2.92 (m, 2H), 2.78 (dt, J=14.2, 2.3 Hz, 2H), 2.21 (td, J=5.5, 2.3 Hz, 1H), 1.76-1.67 (m, 2H), 1.46-1.38 (m, 1H).

Example 14

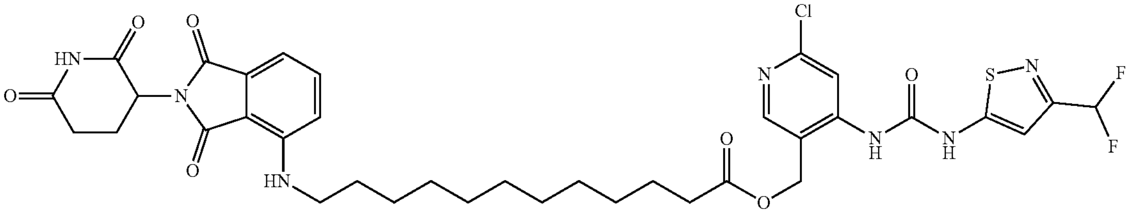 [SMILES: O=C1CCC(N2C(=O)c3cccc(NCCCCCCCCCCCC(=O)OCc4cnc(Cl)cc4NC(=O)Nc4cc(C(F)F)ns4)c3C2=O)C(=O)N1]

According to general procedure A, Yellow powder, 7.7 mg, yield: 66%. MS (ESI) calcd. for C36H40ClF2N7O7S: 787.24, Found: [M+1]788.50, 790.48. 1H NMR (500 MHz, Acetone-d6) δ 10.53 (s, 1H), 9.74 (s, 1H), 8.71 (d, J=4.1 Hz, 1H), 8.22 (s, 1H), 8.18 (s, 1H), 7.45 (dd, J=8.6, 7.1 Hz, 1H), 6.96 (s, 1H), 6.89 (d, J=7.0 Hz, 1H), 6.62 (t, J=54.8 Hz, 1H), 6.28 (t, J=5.8 Hz, 1H), 4.96-4.91 (m, 1H), 3.28-3.20 (m, 2H), 2.89-2.77 (m, 1H), 2.67-2.61 (m, 2H), 2.25 (t, J=7.4 Hz, 2H), 2.10-2.04 (m, 1H), 1.56 (p, J=7.2 Hz, 2H), 1.45 (t, J=7.2 Hz, 2H), 1.30-1.10 (m, 16H).

Example B—Cell Growth ATPlite Assay with Exemplary Compounds of the Disclosure Human MV4; 11 WT, MV4; 11 CRBN KO, and MOLM13 cells were seeded in 384-well plate and treated with indicated compounds for 48 h. ATP level was measured by ATPlite (PerkinElmer) according to manufactures instructions. Experimental groups were measured in quadruplicate and ATP level was normalized to DMSO. $IC_{50}$ was analyzed in GraphPad Prism 7.

TABLE 1

Activity of Exemplary Compounds of the Disclosure

| No. | $IC_{50}$ |
|---|---|
| Example 2 | +++ |
| Example 3 | +++ |
| Example 4 | ++++ |
| Example 7 | ++++ |
| Example 8 | ++++ |
| Example 9 | + |
| Example 10 | ++ |
| Example 11 | + |
| Example 12 | ++++ |
| Example 14 | ++ |

++++ indicates $IC_{50}$ of 0.1 μM or less;
+++ indicates $IC_{50}$ between 0.1 μM and 1 μM;
++ indicates $IC_{50}$ between 1 μM and 10 μM;
++ indicates $IC_{50}$ between 10 μM and 100 μM; and
+ indicates and >$IC_{50}$ 100 μM.

Example C—Immunoblot of SMARCA2 in A549 and MOLM13 Cells

Human A549 were seeded in 6-well plate and treated with Ex. 4 or Ex. 2 for 16, 24 and 40 h. Human MOLM13 were seeded in 6-well plate and treated with Ex. 4 for 6, 10, 16, 24 h. After treatment cells were harvested and lysed in RIPA buffer (Thermo Scientific) with Halt Protease and Phosphatase Inhibitor Cocktail (Thermo Scientific). Protein was extracted and quantified by BCA Protein Assay Kit (Pierce). Protein lysate was separated by NuPAGE 3-8% Tris-Acetate protein gels (Invitrogen) and detected by SMARCA2, PARP and β-ACTIN antibodies (Cell Signaling Technology).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of Formula I:

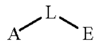

I or a pharmaceutically acceptable salt or stereoisomer thereof, wherein

A is

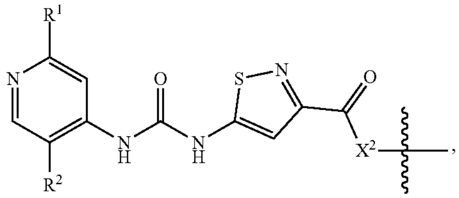

,

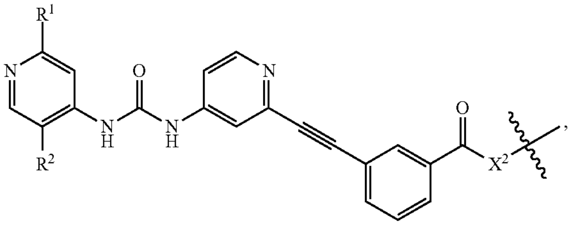

, or

-continued

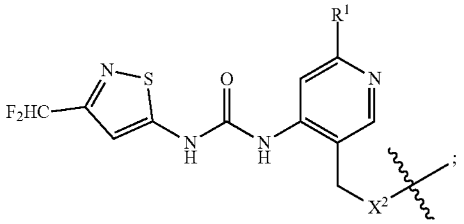

E is

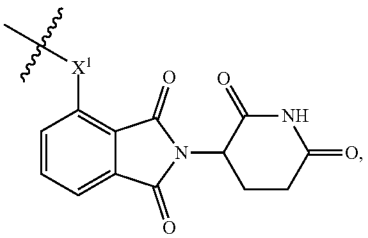

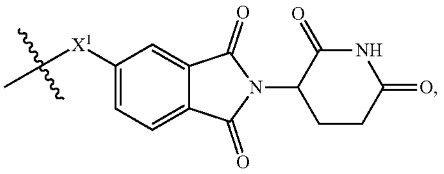

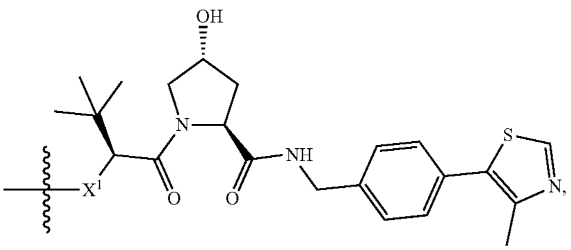

-continued or

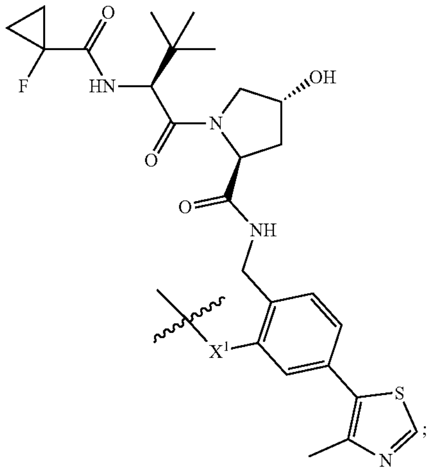

$X^1$ and $X^2$ are each independently selected from O, $NR^3$, and S; or $X^1$ or $X^2$ combine with L to form a heterocyclyl or heteroaryl; or both of $X^1$ and $X^2$ combine with L to form a heterocyclyl or heteroaryl;

L comprises an alkylene, cycloalkylene, heterocyclylene, arylene, or heteroarylene chain, or a combination thereof, comprising 1 to 35 carbon atoms, optionally wherein:

if L comprises an alkylene comprising 1 to 35 $—CH_2—$ moieties, then at least one, but no more than ten, $—CH_2—$ moieties of L are independently replaced with a moiety selected from —C(=O)—, $—C(=O)—NR^4—$, $—NR^4—C(=O)—$, —C(=O)—O—, —O—C(=O)—, $—NR^4—C(=O)—NR^3—$, $—O—C(=O)—NR^4—$, $—NR^4—C(=O)—O—$, —O—, —S—, and $—NR^4—$, provided that the number of $—CH_2—$ moieties of L is larger than the collective number of —C(=O)—, $—C(=O)—NR^4—$, $—NR^4—C(=O)—$, —C(=O)—O—, —O—C(=O)—, $—NR^4—C(=O)—NR_3—$, $—O—C(=O)—NR^4—$, $—NR^4—C(=O)—O—$, —O—, —S—, and $—NR_3—$ moieties of L, and provided there is at least one $—CH_2—$ between each —C(=O)—, $—C(=O)—NR^4—$, $—NR^4—C(=O)—$, —C(=O)—O—, —O—C(=O)—, $—NR^4—C(=O)—NR_3—$, $—O—C(=O)—NR^4—$, $—NR^4—C(=O)—O—$, —O—, —S—, and $—NR^4—$ moiety of L;

$R^1$ is halo;

$R^2$ is H;

$R^3$ and $R^4$ are each independently selected from H and alkyl; and n is 1-5.

2. The compound of claim 1, wherein $R^3$ or $R^4$ is H.

3. The compound of claim 1, wherein the compound is:
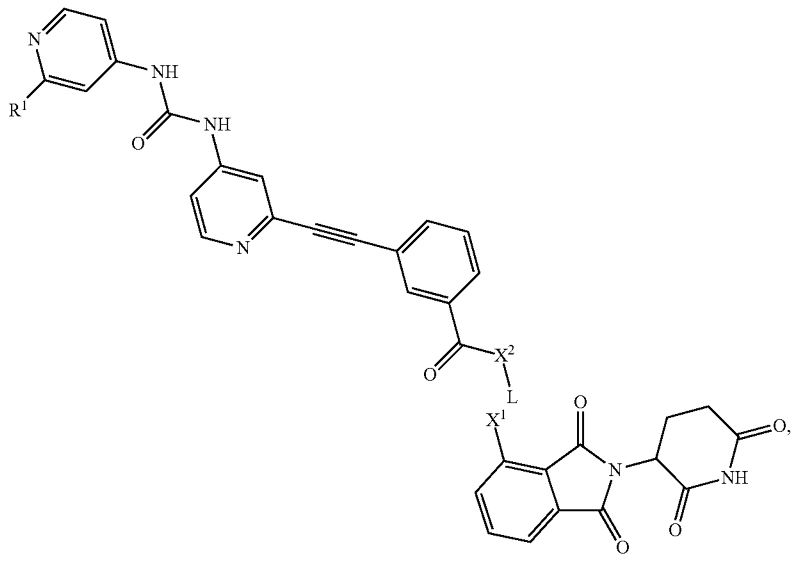
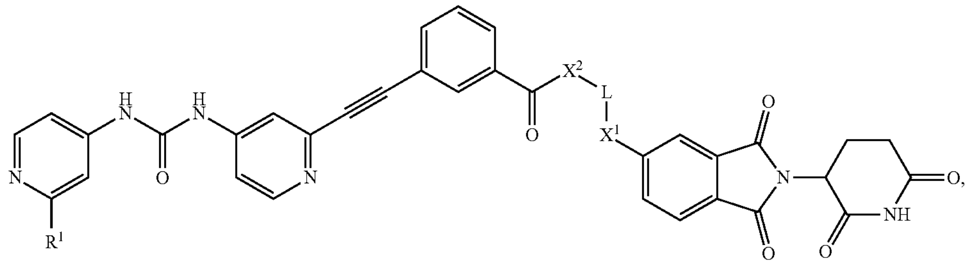
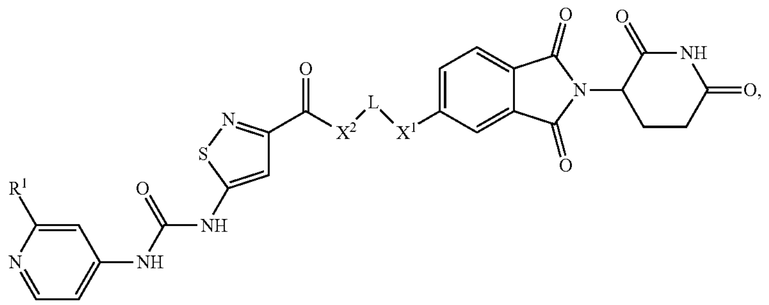
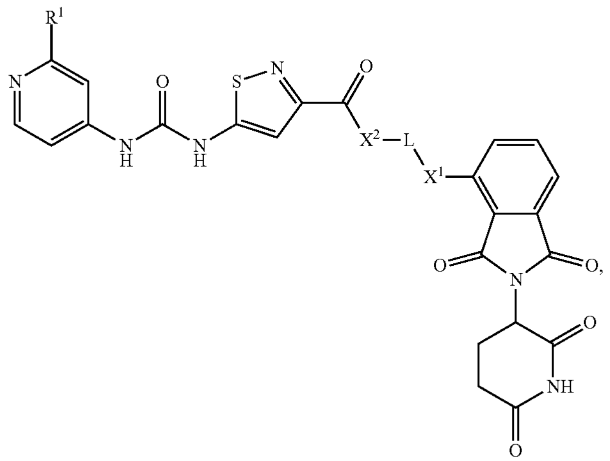

-continued

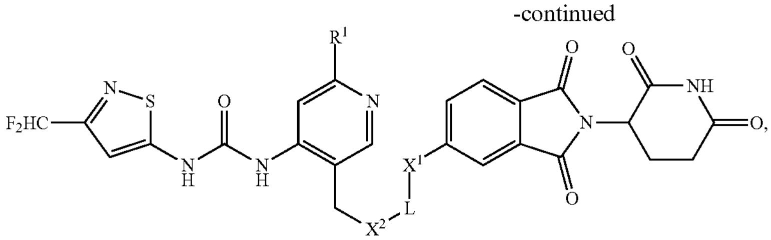

,

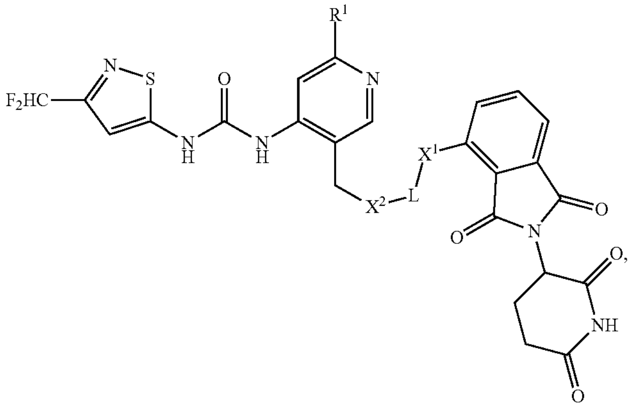

,

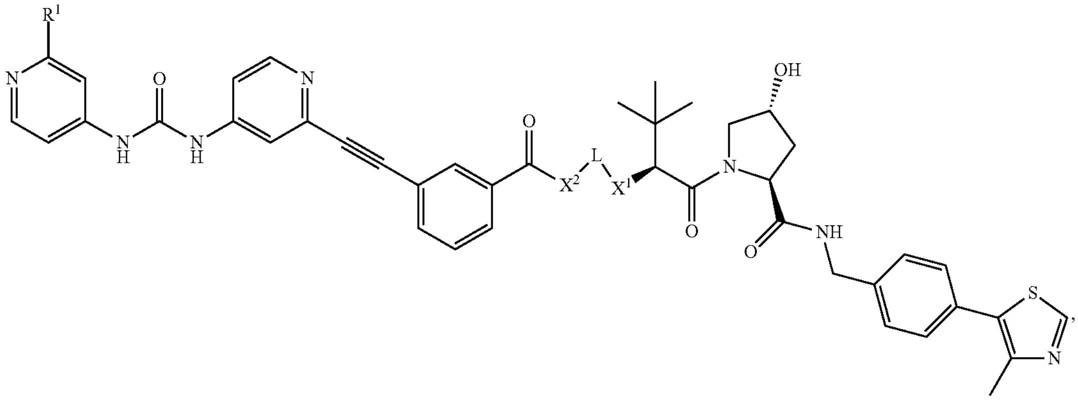

, or

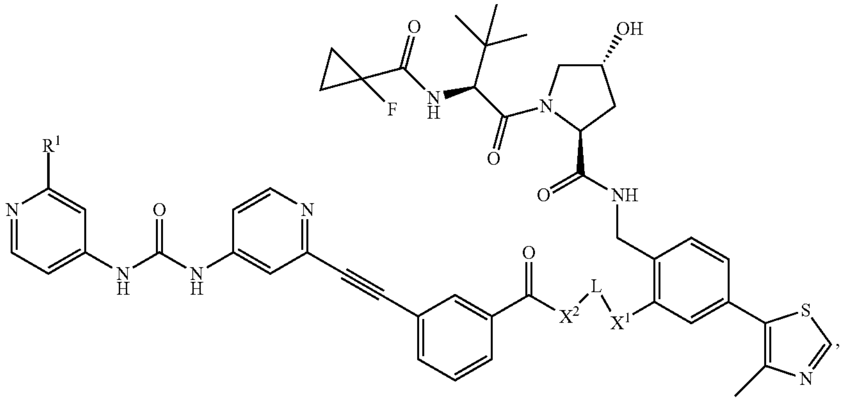

, or a pharmaceutically acceptable salt or stereoisomer thereof.

4. The compound of claim 3, wherein $X^1$ is NH or O.

5. The compound of claim 3, wherein $X^3$ is NH or O.

6. The compound of claim 3, wherein $X^2$ is NH or O.

7. The compound of claim 3, wherein $X^2$ combines with L to form a heterocyclyl.

8. The compound of claim 3, wherein L is alkylene or cycloalkylene.

9. The compound of claim 8, wherein the alkylene comprises 2-25 carbon atoms.

10. The compound of claim 7, wherein the heterocyclyl is piperidinyl.

11. The compound of claim 8, wherein the cycloalkylene is cyclohexylene.

12. The compound of claim 2, wherein $R^1$ is fluoro or chloro.

13. The compound of claim 8, wherein at least one, but no more than five methylene moieties of the alkylene are replaced with an amide moiety or an oxygen atom.

14. The compound of claim 8, wherein one, two, three, or six methylene moieties of the alkylene are replaced with one, two, three, or six amide moieties.

15. The compound of claim 13, wherein at least one, but no more than five methylene moieties of the alkylene are replaced with an amide moiety, and the amide moieties are separated by at least one carbon atom.

16. The compound of claim 1, wherein the compound is selected from:

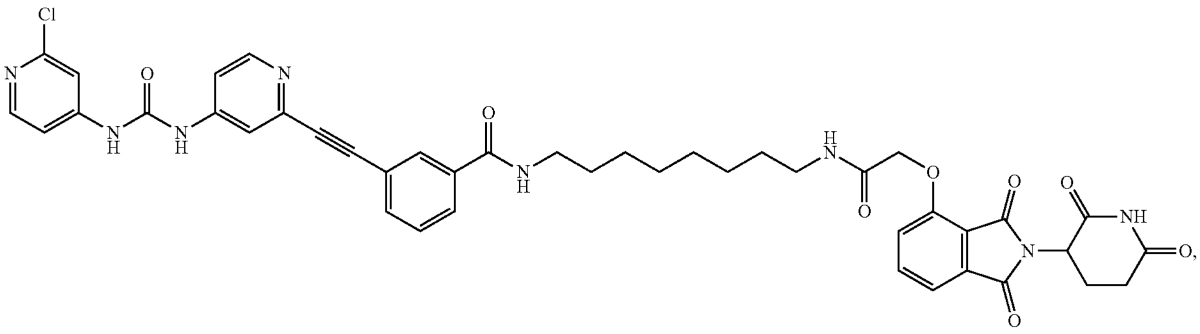
,

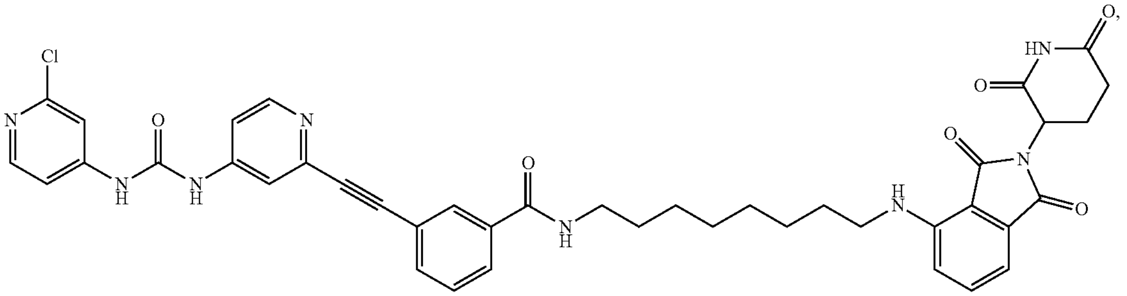
,

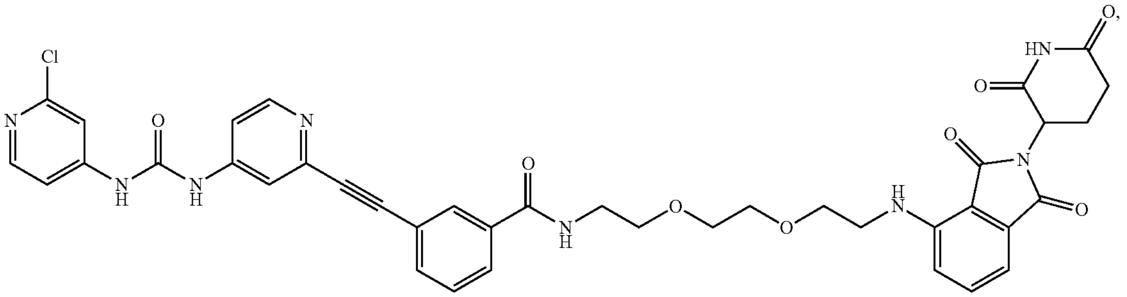
,

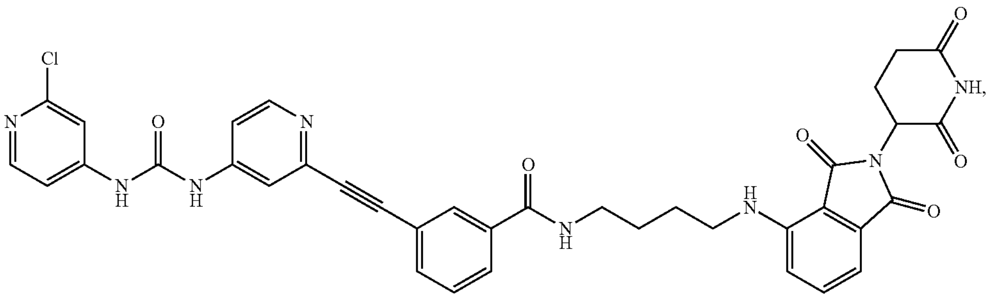
,

-continued
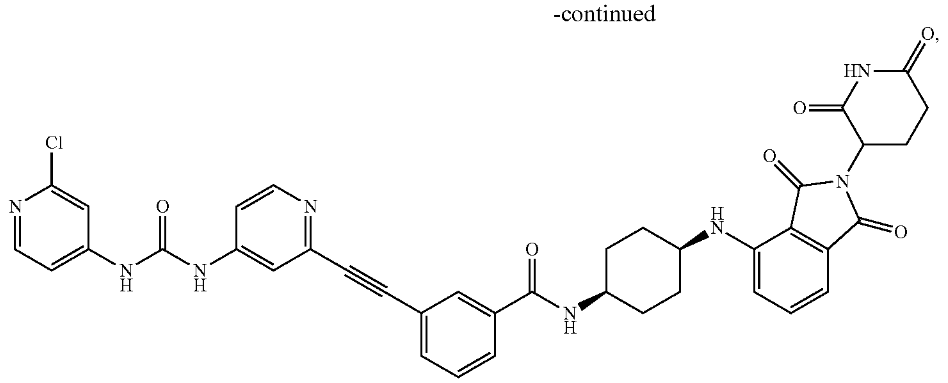
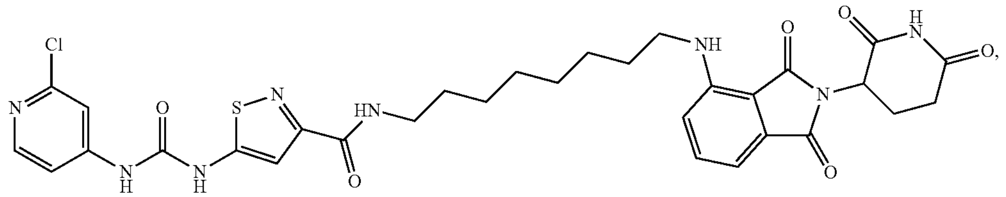
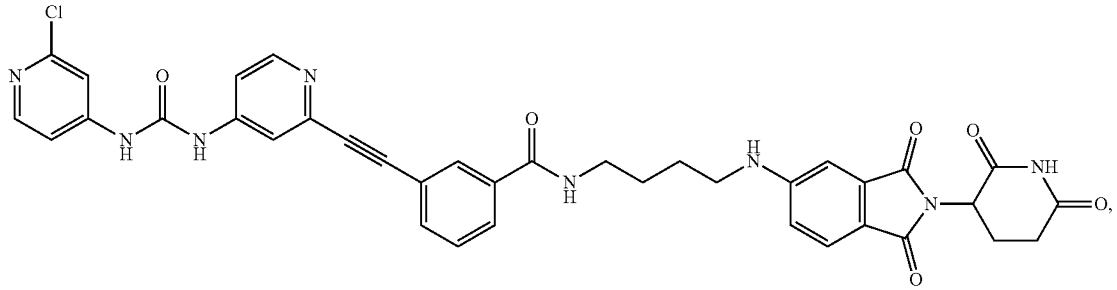
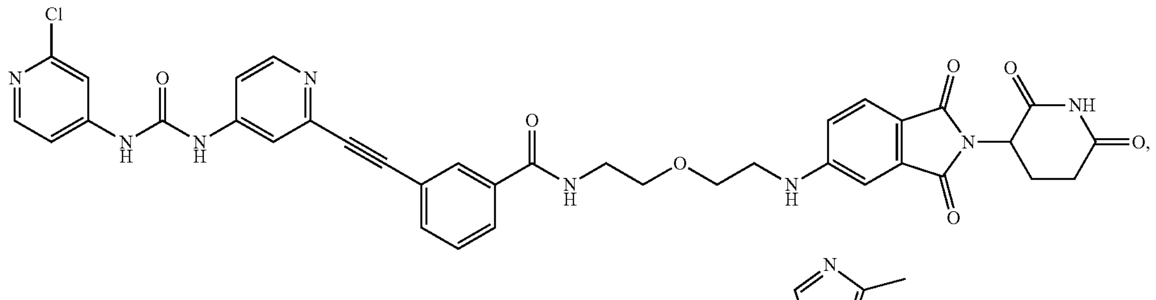
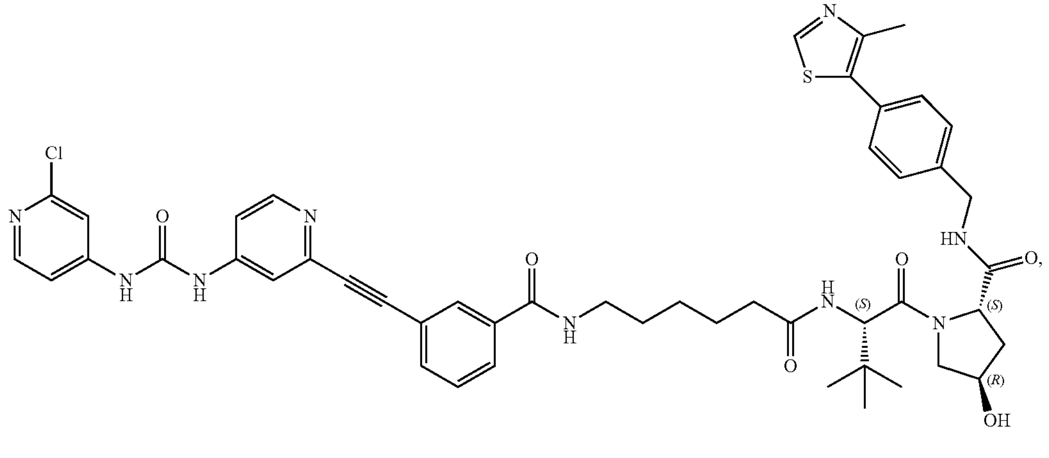

-continued
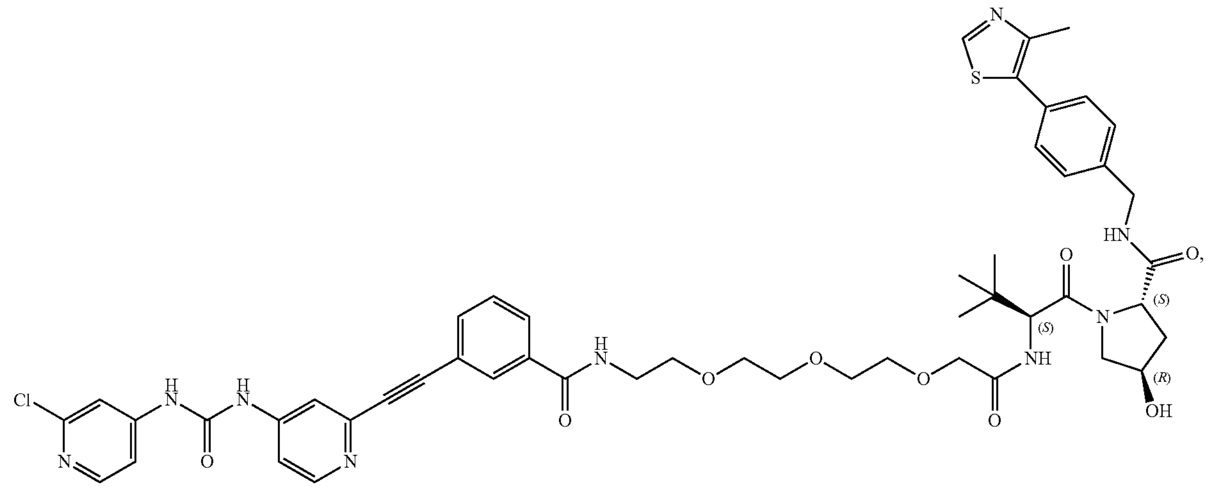
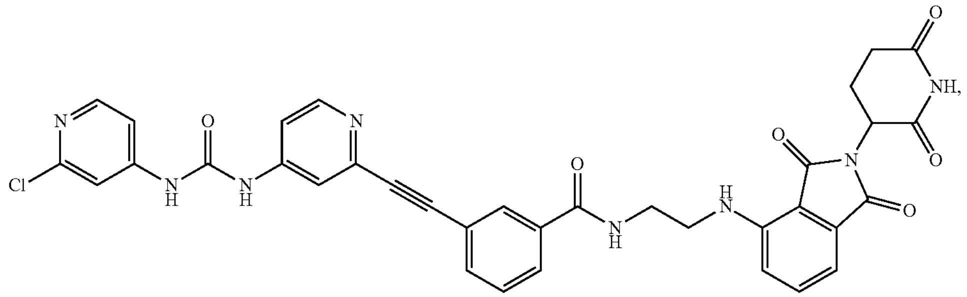
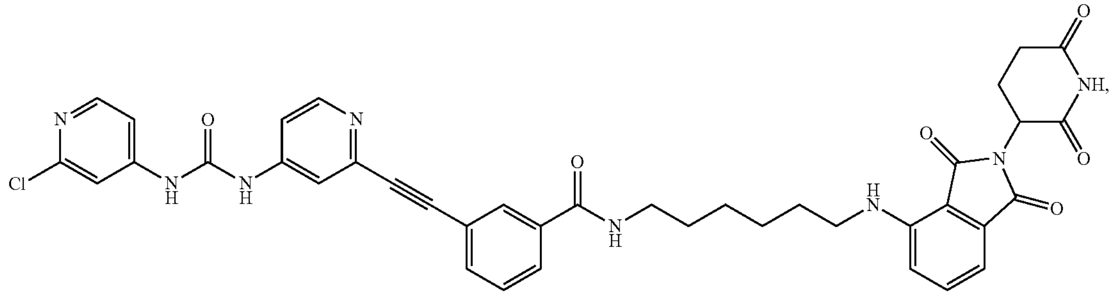
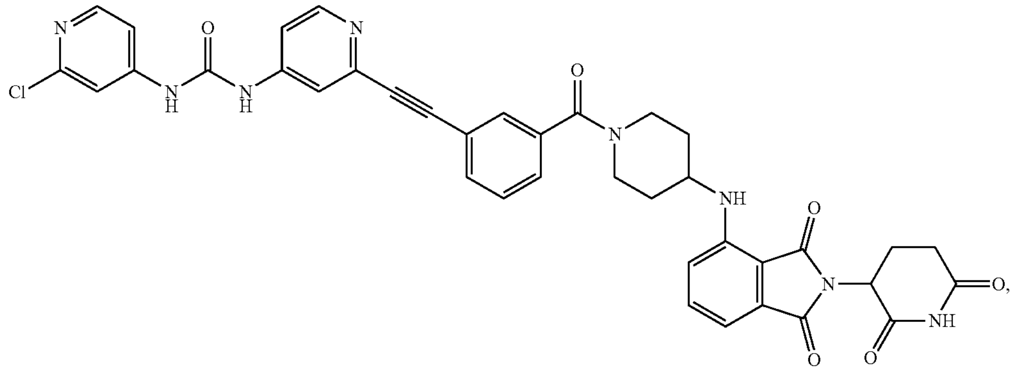
and
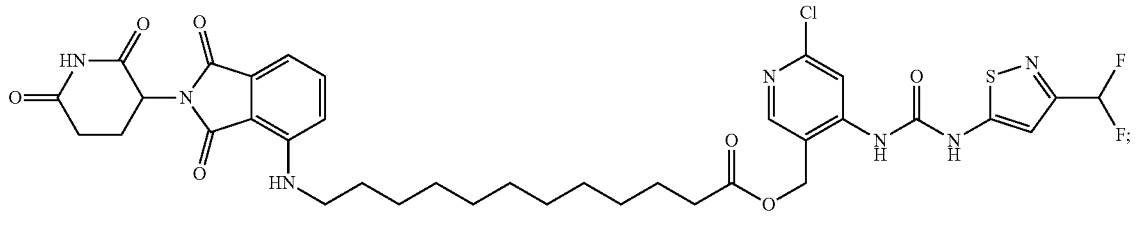

or a pharmaceutically acceptable salt or stereoisomer thereof.

17. A composition comprising the compound or a pharmaceutically acceptable salt or stereoisomer thereof of claim 1 and at least one pharmaceutically acceptable excipient.

* * * * *